United States Patent
Lorens et al.

(10) Patent No.: US 7,566,546 B2
(45) Date of Patent: Jul. 28, 2009

(54) MODULATORS OF ANGIOGENESIS AND TUMORIGENESIS

(75) Inventors: James Lorens, Bones (NO); Sacha J. Holland, San Francisco, CA (US); Weiduan Xu, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 116 days.

(21) Appl. No.: 11/060,659

(22) Filed: Feb. 16, 2005

(65) Prior Publication Data

US 2005/0250163 A1  Nov. 10, 2005

Related U.S. Application Data

(60) Provisional application No. 60/545,981, filed on Feb. 17, 2004.

(51) Int. Cl.
*G01N 33/567* (2006.01)
*G01N 33/53* (2006.01)
*G01N 33/573* (2006.01)

(52) U.S. Cl. .................. 435/7.21; 435/6; 435/7.93; 435/194

(58) Field of Classification Search .............. None
See application file for complete search history.

(56) References Cited

U.S. PATENT DOCUMENTS 6,653,014 B2 * 11/2003 Anderson et al. .......... 429/122

FOREIGN PATENT DOCUMENTS

WO    WO 2005/080984 A1    9/2005

OTHER PUBLICATIONS

Ngo et al., in The Protein Folding Problem and Tertiary Structure Prediction, 1994, Merz, et al., (ed.), Birkhauser, Boston, MA, pp. 433 and 492-495.*
Burden et al, Biochemistry 38: 15141-15149, 1999.*
Nakajima et al, Eur J Pharmacology 459: 113-120, 2003.*
Griffioen et al, Pharmacological Reviews 52(2): 237-268, 2000.*
Paulhe et al, J Biol chem. 276(5): 41832-41840, 2001.*
Minogue et al, J Biol Chem 276(20): 16635-16640, 2001.*
Auerbach et al, Cancer and Metastasis Reviews 19: 167-172, 2000.*
Boger, Dale L. et al.; "Identification of a Novel Class of Small-Molecule Antiangiogenic Agents through the Screening of Combinatorial Libraries Which Function by Inhibiting the Binding and Localization of Proteinase MMP2 to Integrin $\alpha_v\beta_3$"; 2001, *J. Am Chem. Soc.*, vol. 123, pp. 1280-1288.
Cohen, Louis H. et al.; "Inhibitors of Prenylation of Ras and Other G-proteins and Their Application as Therapeutics"; 2000, *Biochemical Pharmacology*, vol. 60, pp. 1061-1068.

* cited by examiner

*Primary Examiner*—Phuong Huynh
(74) *Attorney, Agent, or Firm*—Klarquist Sparkman, LLP

(57) ABSTRACT

The present invention relates to regulation of angiogenesis and tumorigenesis. The invention further relates to methods for identifying and using agents, including small organic molecules, antibodies, peptides, cyclic peptides, nucleic acids, antisense nucleic acids, RNAi, and ribozymes, that modulate angiogenesis via modulation of endothelial cell haptotaxis; as well as to the use of expression profiles and compositions in diagnosis and therapy of angiogenesis and cancer.

8 Claims, 33 Drawing Sheets

Haptotaxis Hits

| Clone # | Identity | Orientation | Classification |
|---|---|---|---|
| GH1-68 | ZIP kinase | Sense, 3'UTR | enzyme / kinase |
| GH2-493 | Phosphatidylinositol 4-kinase Beta | Antisense | enzyme / kinase |
| GH2-551 | Phosphatidylinositol 4-kinase Type II | Antisense | enzyme / kinase |
| GH1-149 | Novel (AL137257.1) / hKIS kinase | Sense, 3'UTR | enzyme / kinase |
| GH2-407 | MAP/ERK Kinase Kinase 3 (MAP3K3) (alternative spliced)? | Spense | enzyme / kinase |
| GH2-617 | SHIP2 inositol phosphatase | Antisense | enzyme / phosphatase |
| GH1-27 | Deoxycytidylate Deaminase | Spense | enzyme / deaminase |
| GH1-173 | Transglutaminase 2 | Antisense | enzyme / transglutaminase |
| GH2-477 / GH1-212 | Delta7-Sterol Reductase | Spense | enzyme / reductase |
| GH2-322 | Protein Geranylgeranyltransferase Type I | Antisense | enzyme / transferase |
| GH2-454 | Glucosamine-6-sulfatase (KIAA1247 protein); | Antisense | enzyme / sulfatase |
| GH2-468 | Carbohydrate (keratan sulfate Gal-6) sulfotransferase 1 (CHST1) | Spense | enzyme / transferase |
| GH2-569 | Heat Shock Protein 105 kDa Beta | Antisense | enzyme / ATPase |
| GH2-596 / GH2-550 | UCH-L1 Ubiquitin Carboxyl-Terminal Hydrolase | Antisense | enzyme / hydrolase |
| GH2-784 | Ubiquitin-Conjugating Enzyme E2M | | false annotation |
| GH2-440 | Equilibrative Nucleoside Transporter 1 (hENT1/SLC29A1) | Spense | transporter |
| GH2-779 | Novel LIV-1-related 6TM protein (6TM ZIP Zinc transporter domain) | Spense | transporter |
| GH1-204 | Plexin A2 | Spense | receptor |
| GH2-439 | Frizzled-4 | Spense | secreted |
| GH2-356 | Stathmin 1/Oncoprotein1 adapter (phospho-Ser) | Spense | adapter |
| GH2-508 | Homo sapiens RNA-binding protein G3BP-2 (G3BP2) (AF145284) | Antisense | RNA binding protein |

FIG. 3

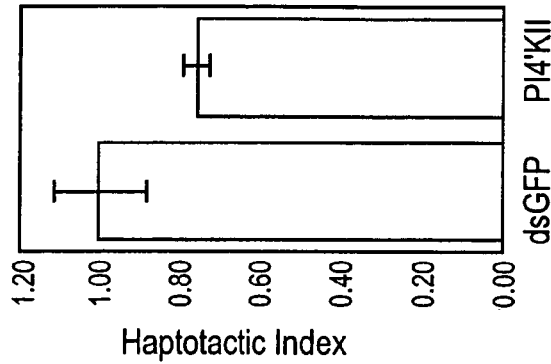
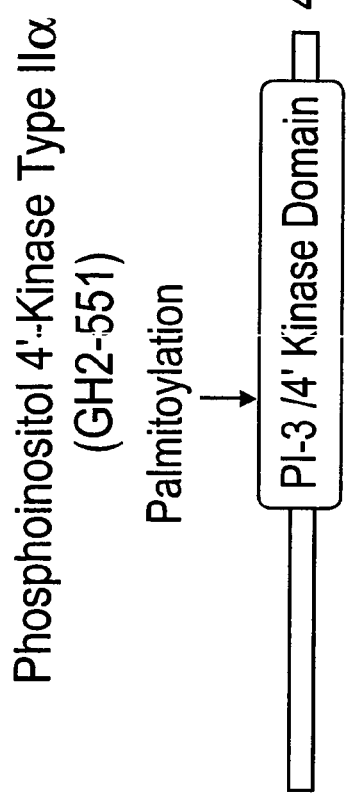
FIG. 5

Delta7-Dehydrocholesterol Reductase (GH2-477)
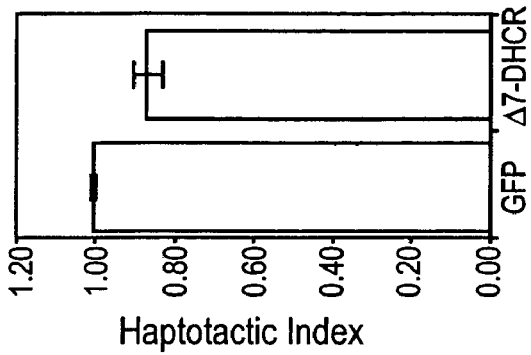
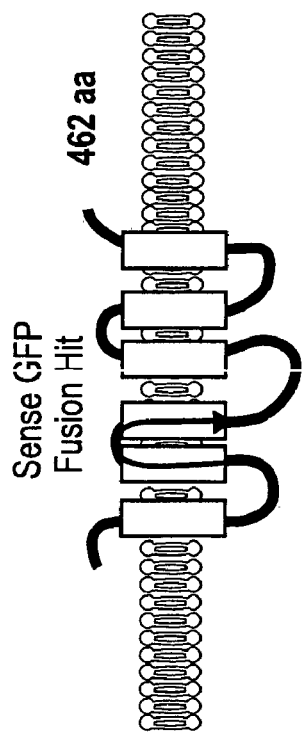
- Sense hit
- Predicted 6-9 membrane spanning regions
- Catalyses last step in cholesterol biosynthesis
- Mutations reducing catalytic activity of Δ7-DHCR associated with Smith-Lemli Opitz Syndrome
- Δ7-DHCR inhibitory compounds severely impair brain development
FIG. 6

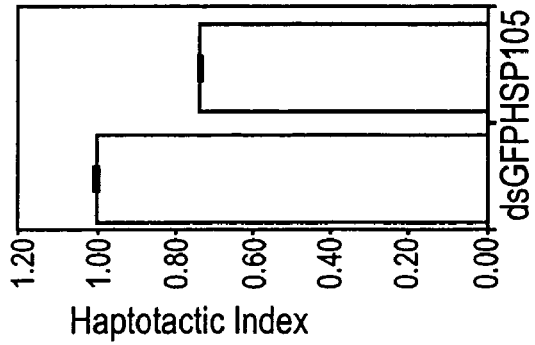
HSP105 (GH2-569)
HSP70 Domain — 814 aa
- Antisense hit
- Chaperone. Prevents aggregation of thermally denatured proteins
- Binds to and regulates activity of HSP-70
- Colocalizes with and prevents heat shock-induced disorganization of microtubules
- Mouse HSP-105 has no ATPase activity
FIG. 7

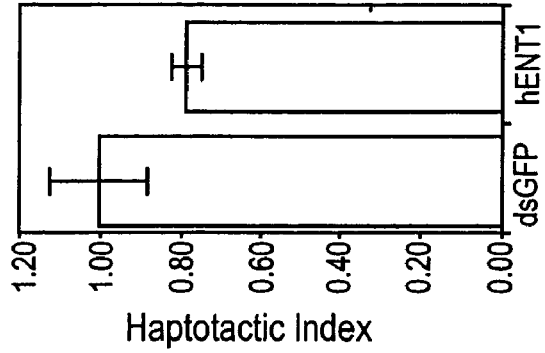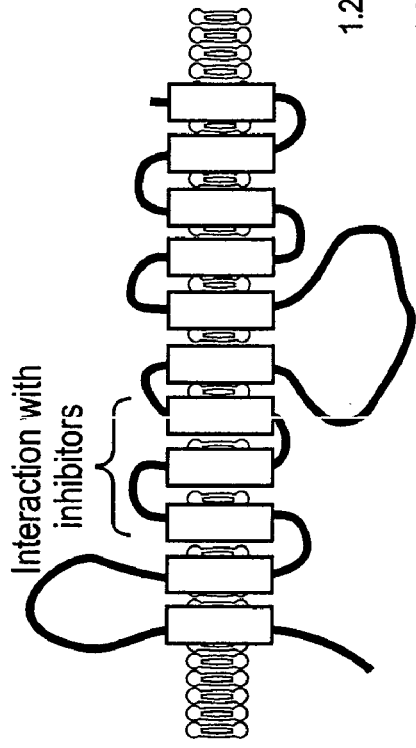
hENT1 / SLC29A1 (GH2-440)
- Sense hit, 3'UTR
- Equilibrative nucleoside transporter
- Appears to be the predominant nucleoside transporter in most cell types
- Involved in nucleoside salvage; transports adenosine, uridine and cytidine and cytotoxic anti-cancer / antiviral nucleoside analogue drugs
- Inhibited by nitrobenzylthioinosine (NBMPR), Dilazep and draflazine
FIG. 9

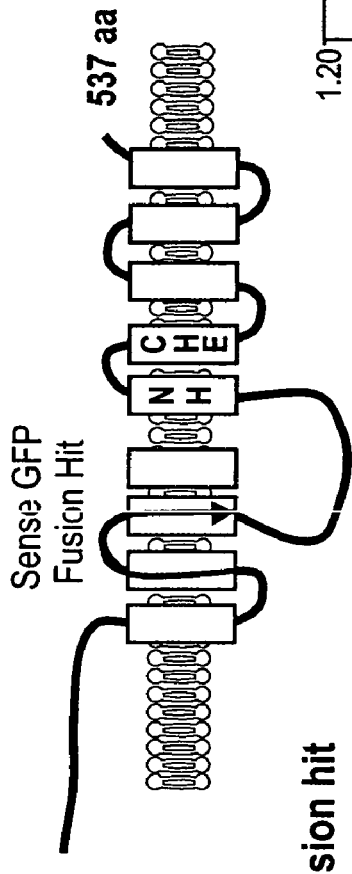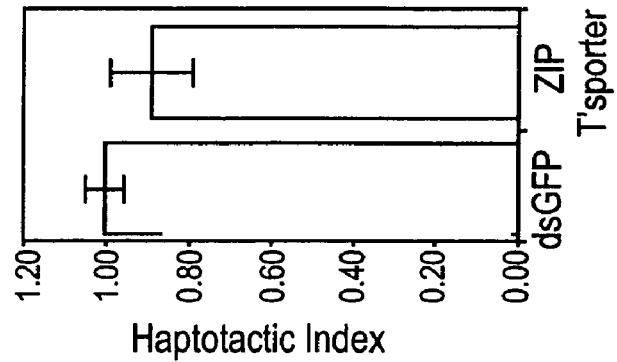

Novel 6 TM ZIP Zinc Transporter (GH2-779)

- Sense GFP fusion hit
- May contain 6 or 8 TM domains
- Related to LIV-1 metastatic breast cancer-associated transporter
- Lacks first H of HXXHE Zn-binding "metalloprotease" sequence and is inactive for Zn transport
- Highly expressed in Colon, Gastroesophagal, Kidney and Liver carcinoma (SOURCE)
- Concentrated in lamellipodia, colocalizes with F-actin

FIG. 10

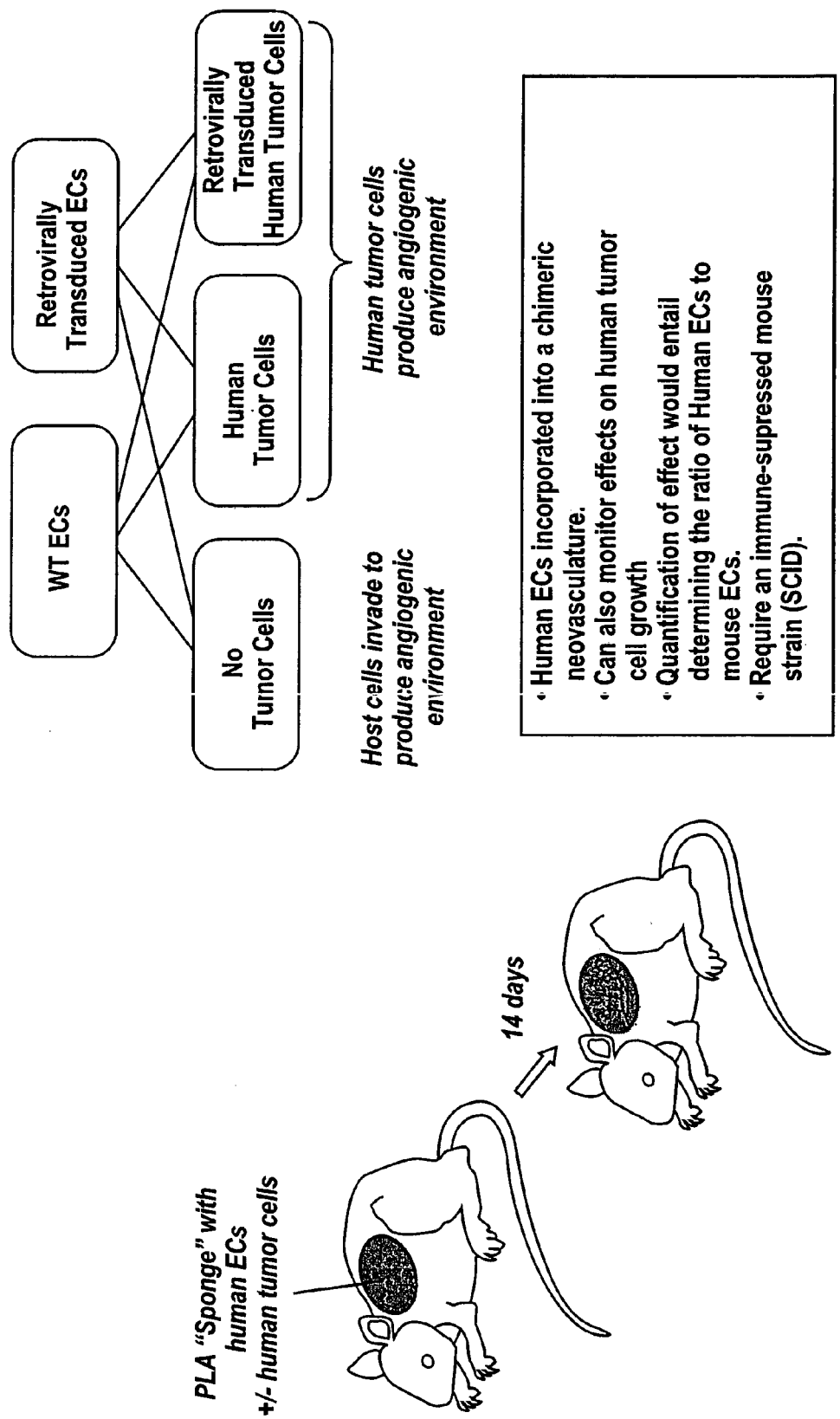

Figure 17A

Phosphatidylinositol 4-kinase beta

Protein accession number NP_002641
Nucleic acid accession numbers: BC040300.1|, NM_002651.1|

>BC040300.1| Homo sapiens, Similar to phosphatidylinositol 4-kinase, catalytic, beta polypeptide, clone MGC:42391 IMAGE:4821417, mRNA, complete cds
Length = 3614

Identities = 344/347 (99%), Gaps = 3/347 (0%)
Strand = Plus / Plus

```
Query: 1     cagcaaggttctcagcttccttgcttccatggctccagcaccattcgaaacctcaaagag 60
             ||||||||||||||||||||||||||||||||||||||||||||||||||||||||||||
Sbjct: 2691  cagcaaggttctcagcttccttgcttccatggctccagcaccattcgaaacctcaaagag 2750

Query: 61    aggttccacatgagcatgactgaggagcagctgcagctgctggtggagcagatggtggat 120
             ||||||||||||||||||||||||||||||||||||||||||||||||||||||||||||
Sbjct: 2751  aggttccacatgagcatgactgaggagcagctgcagctgctggtggagcagatggtggat 2810

Query: 121   ggcagtatgcggtctatcaccaccaaactctatgacggcttccagtacctcaccaacggc 180
             ||||||||||||||||||||||||||||||||||||||||||||||||||||||||||||
Sbjct: 2811  ggcagtatgcggtctatcaccaccaaactctatgacggcttccagtacctcaccaacggc 2870

Query: 181   atcatgtgacacgctcctcagccca-gagtggtgggggtccagggcaccctccctagag 239
             ||||||||||||||||||||||||| ||||||||||||||||||||||||||||||||||
Sbjct: 2871  atcatgtgacacgctcctcagcccaggagtggtgggggtccagggcaccctccctagag 2930

Query: 240   ggccttgtctgagaaaccccaaaccaggaaaccccacctaccc-accatccaccc-agg 297
             |||||||||||||||||||||||||||||||||||||||||||| ||||||||||| |||
Sbjct: 2931  ggccttgtctgagaaaccccaaaccaggaaaccccacctacccaaccatccacccaagg 2990

Query: 298   gaaatggaaggcaagaaacacgaaggatcatgtggtaactgcgagag 344
             |||||||||||||||||||||||||||||||||||||||||||||||
Sbjct: 2991  gaaatggaaggcaagaaacacgaaggatcatgtggtaactgcgagag 3037
```

Figure 17B

Phosphatidylinositol 4-kinase type II

Protein accession number NP_060895
Nucleic acid accession numbers NM_018425.2|

>NM_018425.2| Homo sapiens phosphatidylinositol 4-kinase type II (PI4KII), mRNA
Length = 4185

Identities = 250/252 (99%), Gaps = 1/252 (0%)
 Strand = Plus / Minus

```
Query: 77    ggccagtgtccgagttcagctgcatgtgattgtcggggctgggattggggcaggcaggcg 136
             |||||||||||||| |||||||||||||||||||||||||||||||||||||||||||||
Sbjct: 3231  ggccagtgtccgagt-cagctgcatgtgattgtcggggctgggattggggcaggcaggcg 3173

Query: 137   agctgtaccttcgtccacagggcatgcacatccagctctcagaaattcttcctgtcagcc 196
             ||||||||||||||||||||||||||||||||||||||||||||||||||||||||||||
Sbjct: 3172  agctgtaccttcgtccacagggcatgcacatccagctctcagaaattcttcctgtcagcc 3113

Query: 197   aggtggaagcccgggacaagtggactcttggtggctggactggaaggggaccggcgggga 256
             ||||||||||||||||||||||||||||||||||||||||||||||||||||||||||||
Sbjct: 3112  aggtggaagcccgggacaagtggactcttggtggctggactggaaggggaccggcgggga 3053

Query: 257   ccagcctggaccagctgaccagagggctgcacatctctgctctgcagcagggcaagcaga 316
             |||||||||||||||||||||||||||||||||||||||||||||| ||||||||||||
Sbjct: 3052  ccagcctggaccagctgaccagagggctgcacatctctgctctgcagccgggcaagcaga 2993

Query: 317   ggacatgcagcc 328
             ||||||||||||
Sbjct: 2992  ggacatgcagcc 2981
```

Figure 17C

MAP/ERK kinase kinase 3

Protein accession number AAH10464
Nucleic acid accession numbers: AC046185.14|, BC010464
Note: Maps to just outside the identified coding region of MAP3K3 (NM_002401, NP_002392).

>AC046185.14| Homo sapiens chromosome 17, clone RP11-51F16, complete sequence,
Length = 173637

Identities = 337/340 (99%), Gaps = 1/340 (0%)
Strand = Plus / Minus

```
Query: 1      ctggttttgcagaagtgtgtgtcgcatgcgccagttgggcctggaccctcctgtgtccat 60
              ||||||||||||||||||||||||||||||||||||||||||||||||||||||||||||
Sbjct: 34218  ctggttttgcagaagtgtgtgtcgcatgcgccagttgggcctggaccctcctgtgtccat 34159

Query: 61     ccctgttccccaggggctctatcagccctgtacccacactgccctctgaagaca-ca 119
              |||||||||||||||||||||||||||||||||||||||||||||||||||||||| ||
Sbjct: 34158  ccctgttccccaggggctctatcagccctgtacccacactgccctctgaagacaaca 34099

Query: 120    caggctcctgcttccacctcggcccttgcccagggtggggcctggccctcatcttgacca 179
              ||||||||||||||||||||||||||||||||||||||||||||||||||||||||||||
Sbjct: 34098  caggctcctgcttccacctcggcccttgcccagggtggggcctggccctcatcttgacca 34039

Query: 180    aagctgctgtgtggcagctcggcctctctacgacccatcttggtggctgcacactcttc 239
              |||||||||||||||||||||||||||||||||||||||||||||||||||||||||||
Sbjct: 34038  aagctgctgtgtggcagctcggcctctctacgacccatcttggtggctgcacactcttc 33979

Query: 240    ctggcccgcacccccatccccagtccctgttccccaagaggatacagagcacggtgcttg 299
              |||||||||||||||||||||||||||||||||||||||||||||||||||||||||| |
Sbjct: 33978  ctggcccgcaccccatccccagtccctgttccccaagaggatacagagcacggtgctgg 33919

Query: 300    ctgactcaactgtgcgtcccatgttcagggtcttacagag 339
              |||||||||||||||||||||| |||||||||||||||||
Sbjct: 33918  ctgactcaactgtgcgtcccaggttcagggtcttacagag 33879
```

Figure 17D

SHIP2 inositol phosphatase
Protein accession number NP_001558
Nucleic acid accession numbers: NM_001567.2

>NM_001567.2| Homo sapiens inositol polyphosphate phosphatase-like 1 (INPPL1), mRNA
Length = 4737

Identities = 216/218 (99%), Gaps = 1/218 (0%)
  Strand = Plus / Plus

```
Query:   19 ggggagggagatgcaccttaatattattggggttggttggggtggggcaggatctcagcc   78
            ||||||||||| |||||||||||||||||||||||||||||||||||||||||||||||
Sbjct: 4485 ggggagggaga-gcaccttaatattattggggttggttggggtggggcaggatctcagcc 4543

Query:   79 ataaagtgccagtttgcttagttctcactgtctcctggtctgtgctgccctgctctgggg  138
            ||||||||||||||||||||||||||||||||||||||||||||||||||||||||||||
Sbjct: 4544 ataaagtgccagtttgcttagttctcactgtctcctggtctgtgctgccctgctctgggg 4603

Query:  139 atgcacggcggcagggtggggagggaggttcctcgcaggtctcagcccgggacagggtc  198
            ||||||||||||||||||||||||||||||||||||||||||||||||||||||||||||
Sbjct: 4604 atgcacggcggcagggtggggagggaggttcctcgcaggtctcagcccgggacagggtc 4663

Query:  199 ttgcaagcagcctcctgggcagtcgtaagggttacggc  236
            |||||||||||||||||||||||||||||||| ||||
Sbjct: 4664 ttgcaagcagcctcctgggcagtcgtaagggttgcggc 4701
```

Figure 17E

Protein geranylgeranyltransferase type I
Protein accession number AAA35888
Nucleic acid accession numbers: |HUMGGTBS >gi|466490|gb|L25441.1|HUMGGTBS Human geranylgeranyltransferase type I beta-
subunit mRNA, complete, cds
Length = 1969

Identities = 270/270 (100%)
 Strand = Plus / Minus

```
Query: 82  ccaggtatgaagagcctcggaaaccacagcgatttagatttgatctgtcttctgtgggaa 141
           ||||||||||||||||||||||||||||||||||||||||||||||||||||||||||||
Sbjct: 616 ccaggtatgaagagcctcggaaaccacagcgatttagatttgatctgtcttctgtgggaa 557

Query: 142 ggacctgcagggaataaatccactctattatatcatctttgttcaccacatctaaggaat 201
           ||||||||||||||||||||||||||||||||||||||||||||||||||||||||||||
Sbjct: 556 ggacctgcagggaataaatccactctattatatcatctttgttcaccacatctaaggaat 497

Query: 202 ccaacatatccagcccggagagtgcaaaaaatgcaattgtcaacctgcttgtctcgagtg 261
           ||||||||||||||||||||||||||||||||||||||||||||||||||||||||||||
Sbjct: 496 ccaacatatccagcccggagagtgcaaaaaatgcaattgtcaacctgcttgtctcgagtg 437

Query: 262 aagaatagcgctccggcaaaacctggaggcagcgctggaaaaatcgcacgtgccgatccc 321
           ||||||||||||||||||||||||||||||||||||||||||||||||||||||||||||
Sbjct: 436 aagaatagcgctccggcaaaacctggaggcagcgctggaaaaatcgcacgtgccgatccc 377

Query: 322 gtaagaaatccagccgctctccctcaccgc 351
           ||||||||||||||||||||||||||||||
Sbjct: 376 gtaagaaatccagccgctctccctcaccgc 347
```

Figure 17F

Glucosamine-6-sulfatase
Protein accession number AAM76861
Nucleic acid accession numbers: AY101176.1, AB033073.2

>gi|27356933|gb|AY101176.1| Homo sapiens extracellular sulfatase SULF-2 mRNA, complete cds
Length = 4279

Identities = 174/175 (99%), Gaps = 1/175 (0%)
 Strand = Plus / Minus

```
Query: 84    acgtgttgtccagctcgcccgtctcaaccagcatgttgtaaatcgtctccatggagtcgt 143
             ||||||||||||||||||||||||||||||||||||||||||||||||||||||||||||
Sbjct: 1600  acgtgttgtccagctcgcccgtctcaaccagcatgttgtaaatcgtctccatggagtcgt 1541

Query: 144   c-accgacatgagggtctgcaagcgcttccgctggagcatgttggtgaattccatgtgga 202
             | ||||||||||||||||||||||||||||||||||||||||||||||||||||||||||
Sbjct: 1540  ccaccgacatgagggtctgcaagcgcttccgctggagcatgttggtgaattccatgtgga 1481

Query: 203   tgggcttcatgggccccgtgtagcgcatgatccagtgtttgtccgggttgggcgc 257
             |||||||||||||||||||||||||||||||||||||||||||||||||||||||
Sbjct: 1480  tgggcttcatgggccccgtgtagcgcatgatccagtgtttgtccgggttgggcgc 1426
```

Figure 17G

Carbohydrate sulfotransferase 1
Protein accession number NP_003645
Nucleic acid accession numbers: NM_003654.1|

>gi|4502840|ref|NM_003654.1| Homo sapiens carbohydrate (keratan sulfate Gal-6)
sulfotransferase 1 (CHST1), mRNA
Length = 2415

Identities = 457/458 (99%), Gaps = 1/458 (0%)
 Strand = Plus / Plus

```
Query:  71  agcttggagcagtccctctttgacctcacccCttggagaagcagccccatgaaggtgccc  130
            ||||||||||||||||||||||||||||||||||||||||||||||||||||||||||||
Sbjct: 303  agcttggagcagtccctctttgacctcacccCttggagaagcagccccatgaaggtgccc  362

Query: 131  agccatgcaatgttcctggaaggccgtcctcctccttgccctggcctccattgccatcca  190
            ||||||||||||||||||||||||||||||||||||||||||||||||||||||||||||
Sbjct: 363  agccatgcaatgttcctggaaggccgtcctcctccttgccctggcctccattgccatcca  422

Query: 191  gtacacggccatccgcaccttcaccgccaagtcctttcacacctgccccgggctggcaga  250
            ||||||||||||||||||||||||||||||||||||||||||||||||||||||||||||
Sbjct: 423  gtacacggccatccgcaccttcaccgccaagtcctttcacacctgccccgggctggcaga  482

Query: 251  ggccgggctggccgagcgactgtgcgaggagagccccaccttcgcctacaacctctcccg  310
            ||||||||||||||||||||||||||||||||||||||||||||||||||||||||||||
Sbjct: 483  ggccgggctggccgagcgactgtgcgaggagagccccaccttcgcctacaacctctcccg  542

Query: 311  caagacccacatcctcatcctggccaccacgcgcagcggctcctccttcgtgggccagct  370
            ||||||||||||||||||||||||||||||||||||||||||||||||||||||||||||
Sbjct: 543  caagacccacatcctcatcctggccaccacgcgcagcggctcctccttcgtgggccagct  602

Query: 371  cttcaaccagcacctggacgtcttctacctgtttgagcccctctaccacgtccagaacac  430
            ||||||||||||||||||||||||||||||||||||||||||||||||||||||||||||
Sbjct: 603  cttcaaccagcacctggacgtcttctacctgtttgagcccctctaccacgtccagaacac  662

Query: 431  gctcatccccgcttcacccaggggcaagagcccggccgaccggcgggtcatgctaggcg  490
            |||||||||||||||||||||||| |||||||||||||||||||||||||||||||||||
Sbjct: 663  gctcatccccgcttcaccca-gggcaagagcccggccgaccggcgggtcatgctaggcg  721

Query: 491  ccagccgcgacctcctgcggagcctctacgactgcgac  528
            ||||||||||||||||||||||||||||||||||||||
Sbjct: 722  ccagccgcgacctcctgcggagcctctacgactgcgac  759
```

Figure 17H

Heat shock protein 105 kDa beta
Protein accession number NP_006635
Nucleic acid accession numbers:, BC037553.1| , BC018124, NM_006644.1|

>gi|22902176|gb|BC037553.1| Homo sapiens, Similar to heat shock 105kD, clone
MGC:40320, IMAGE:4540927, mRNA, complete cds
   Length = 3623

Identities = 524/530 (98%), Gaps = 5/530 (0%)
   Strand = Plus / Minus

```
Query: 1    tgaaggggtcat-gaatgctcggccatgaaatcttt-gaagttagacaccgtat-gtttg  57
            |||||||||||| |||||||||||||||||||||||| ||||||||||||||||| |||||
Sbjct: 579  tgaaggggtcattgaatgctcggccatgaaatcttttgaagttagacaccgtattgtttg  520

Query: 58   catgagtgatttgctgatttt-ggctgcaactccgattgttctattttttgatccaaatg  116
            ||||||||||||||||||||| ||||||||||||||||||||||||||||||||||||||
Sbjct: 519  catgagtgatttgctgattttggctgcaactccgattgttctattttttgatccaaatg   460

Query: 117  atatagactgacggggtgcaccggtcgctgaactcattggcgatggtctcgatgcccccg  176
            |||| |||||||||||||||||||||||||||||||||||||||||||||||||||||||
Sbjct: 459  atat-gactgacggggtgcaccggtcgctgaactcattggcgatggtctcgatgcccccg  401

Query: 177  gcccgggctaccgcgatgtagcagctctgcgagcccacgtccaacccaccaccgacatg   236
            ||||||||||||||||||||||||||||||||||||||||||||||||||||||||||||
Sbjct: 400  gcccgggctaccgcgatgtagcagctctgcgagcccacgtccaacccaccaccgacatg   341

Query: 237  gccggctcgcggtccgcctccgcctcgggtctcggtctacgtcctccggcccctgcctg  296
            ||||||||||||||||||||||||||||||||||||||||||||||||||||||||||||
Sbjct: 340  gccggctcgcggtccgcctccgcctcgggtctcggtctacgtcctccggcccctgcctg  281

Query: 297  cttctcctgccgccgctttctgccctggccgcgttctgctccggcccgcggggtctggcc  356
            ||||||||||||||||||||||||||||||||||||||||||||||||||||||||||||
Sbjct: 280  cttctcctgccgccgctttctgccctggccgcgttctgctccggcccgcggggtctggcc  221

Query: 357  gttcctctgacactcagaaggacacacagaccgccgcggcctgtcaggagcctcctactc  416
            |||||||||||||||||||||||||||||||| |||||||||||||||||||||||||||
Sbjct: 220  gttcctctgacactcagaaggacacacagacagccgcggcctgtcaggagcctcctactc  161

Query: 417  ccccggggacagcggcggctggctgataagaaaccctgggagaaagcggggctcagcctc  476
            ||||||||||||||||||||||||||||||||||||||||||||||||||||||||||||
Sbjct: 160  ccccggggacagcggcggctggctgataagaaaccctgggagaaagcggggctcagcctc  101

Query: 477  cgcaggtcgctccgcacctcggggttgcctgcctcactctgccgcggctcg  526
            ||||||||||||||||||||||||||||||||||||||||||||||||||
Sbjct: 100  cgcaggtcgctccgcacctcggggttgcctgcctcactctgccgcggctcg  51
```

Figure 17I

UCH-L1 ubiqiutin carboxyl terminal hydrolase
Protein accession number NP_004172
Nucleic acid accession numbers:, NM_004181.2|

>gi|21361090|ref|NM_004181.2| Homo sapiens ubiquitin carboxyl-terminal esterase
L1 (ubiquitin hiolesterase) (UCHL1), mRNA
Length = 1119

Identities = 310/319 (97%), Gaps = 2/319 (0%)
 Strand = Plus / Minus

```
Query: 22   actgaagcattttagactgcatnnnnnnnntatatattttcatgttgaagggaagagggga 81
            |||||||||||||||||||||||||        ||||||||||||||||||||||||||||
Sbjct: 833  actgaagcattttagactgcatggggggggtatatattttcatgttgaagggaagagggga 774

Query: 82   aatcagcaaagtccctcccacagagcattaggctgccttgcagagagccacggcagagaa 141
            ||||||||||||||||||||||||||||||||||||||||||||||||||||||||||||
Sbjct: 773  aatcagcaaagtccctcccacagagcattaggctgccttgcagagagccacggcagagaa 714

Query: 142  gcggacttctccttgctcacgctcggtgaattctctgcagaccttggcagcgtccttcag 201
            ||||||||||||||||||||||||||||||||||||||||||||||||||||||||||||
Sbjct: 713  gcggacttctccttgctcacgctcggtgaattctctgcagaccttggcagcgtccttcag 654

Query: 202  cagggtgtcctctgaactggcgccatggttcaccggaaaaggcattcgtccatcaagtt- 260
            |||||||||||||||||||||||||||||||||||||||||||||||||||||||||||
Sbjct: 653  cagggtgtcctctgaactggcgccatggttcaccggaaaaggcattcgtccatcaagttc 594

Query: 261  atagaggtgg-catccacgttgttaaacagaataaaatggaaattccacttgtcatctac 319
            |||||||||| |||||||||||||||||||||||||||||||||||||||||||||||||
Sbjct: 593  atagaggtggccatccacgttgttaaacagaataaaatggaaattccacttgtcatctac 534

Query: 320  ccgacattggccttcctgt 338
            |||||||||||||||||||
Sbjct: 533  ccgacattggccttcctgt 515
```

Figure 17J

Equilibrative nucleoside transporter 1
Protein accession number NP_004946
Nucleic acid accession numbers:, BC008954, NM_004955.1

>gi|14286305|gb|BC008954.1|BC008954 Homo sapiens, Similar to solute carrier
family 29 (nucleoside transporters), member 1, clone MGC:3778 IMAGE:3010092,
mRNA, complete cds
Length = 2189

Identities = 157/161 (97%), Gaps = 3/161 (1%)
 Strand = Plus / Minus

```
Query: 45    ggtaagaactgggcatggggagttcgggaggggggacatggagagaacacagaggaggagg 104
             |||||||||||||||||||||||| |||||||||||||||||||||||||||||||||||
Sbjct: 2056  ggtaagaactgggcatggggagtt-ggggaggggggacatggagagaacacagaggaggagg 1998

Query: 105   cgcaggggggagaatggagtatatcaggtcaaaccatacaacggtcagacccagctcctag 164
             ||||||||  ||||||||||||||||||||||||||||||||||||||||||||||||||
Sbjct: 1997  cgcagggg-agaatggagtatatcaggtcaaaccatacaacggtcagacccagctcctag 1939

Query: 165   ccactccagtgacaggcagacagtctgacagacacggacgc 205
             ||||  ||| |||||||||||||||||||||||||||||||
Sbjct: 1938  ccaccccag-gacaggcagacagtctgacagacacggacgc 1899
```

Figure 17K

Novel LIV-1-related 6TM protein
Note: See domain description in NCBI protein listing for first hit below.
Protein accession number AAH15770
Nucleic acid accession numbers: BC015770

>gi|16041778|gb|BC015770.1|BC015770 Homo sapiens, clone MGC:23235 IMAGE:4865469,
mRNA, complete cds
Length = 1755

Identities = 259/265 (97%), Gaps = 4/265 (1%)
 Strand = Plus / Plus

```
Query: 33   gctctggcgattggaaccctctactccaacgccctcttccagctcatcccggag-cattt 91
            |||||||||||||||||||||||||||||||||||||||||||||||||||||| |||||
Sbjct: 711  gctctggcgattggaaccctctactccaacgccctcttccagctcatcccggaggcattt 770

Query: 92   ggtttcaaccctcttgaaagattattatgtctccaagtctgcagtggtgtttggggctt 151
            ||||||||||||| ||| ||||||||||||||||||||||||||||||||||||||||||
Sbjct: 771  ggtttcaaccctctggaa-gattattatgtctccaagtctgcagtggtgtttggggctt 829

Query: 152  ttatcttttcttttcacagagaagatcttgaagattcttcttaagcagaaaaatgagca 211
            ||||||||||||||||||||||||||||||||||||||||||||||||||||||||||||
Sbjct: 830  ttatcttttcttttcacagagaagatcttgaagattcttcttaagcagaaaaatgagca 889

Query: 212  tcatcatggacacagccattatgcctct-agtcgcttccctcc-agaaggaccaggagga 269
            |||||||||||||||||||||||||||| |||||||||||||| ||||||||||||||||
Sbjct: 890  tcatcatggacacagccattatgcctctgagtcgcttccctccaagaaggaccaggagga 949

Query: 270  gggggtgatggagaagccgcagaac 294
            ||||||||||||||||| |||||||
Sbjct: 950  gggggtgatggagaagctgcagaac 974
```

Figure 17L

Frizzled 4
Protein accession number BAA86286
Nucleic acid accession numbers: AB032417.1

>gi|6277265|dbj|AB032417.1| Homo sapiens FZD4 mRNA for WNT receptor Frizzled-4, complete cds
Length = 7392

Identities = 109/109 (100%)
 Strand = Plus / Plus

```
Query: 84    ctttctgttgctgtctcttgccatgcacttgtgcggtgattacacacttgacagtaccag 143
             ||||||||||||||||||||||||||||||||||||||||||||||||||||||||||||
Sbjct: 6455  ctttctgttgctgtctcttgccatgcacttgtgcggtgattacacacttgacagtaccag 6514

Query: 144   gagacaaatgacttacagatcccccgacatgcctcttccccttggcaag 192
             |||||||||||||||||||||||||||||||||||||||||||||||||
Sbjct: 6515  gagacaaatgacttacagatcccccgacatgcctcttccccttggcaag 6563
```

Figure 17M

Stathmin 1
Protein accession number CAA37391
Nucleic acid accession numbers: HSRNSTATH >gi|57869|emb|X53305.1|HSRNSTATH H.sapiens mRNA for stathmin
Length = 1429

Identities = 162/162 (100%)
 Strand = Plus / Plus

Query: 3    actgtattggctctgtgaaaacatatttgtgaaaagagtatgtagtggcttctttgaac 62
            ||||||||||||||||||||||||||||||||||||||||||||||||||||||||||||
Sbjct: 818  actgtattggctctgtgaaaacatatttgtgaaaagagtatgtagtggcttctttgaac 877

Query: 63   tgttagatgctgaatatctgttcacttttcaatcccaattctgtcccaatcttaccagat 122
            ||||||||||||||||||||||||||||||||||||||||||||||||||||||||||||
Sbjct: 878  tgttagatgctgaatatctgttcacttttcaatcccaattctgtcccaatcttaccagat 937

Query: 123  gctactggacttgaatggttaataaaactgcacagtgctgtt 164
            ||||||||||||||||||||||||||||||||||||||||||
Sbjct: 938  gctactggacttgaatggttaataaaactgcacagtgctgtt 979

Figure 17N

Homo sapiens RNA-binding protein G3BP2
Protein accession number NP_036429
Nucleic acid accession numbers: NM_012297.2|

>gi|19923398|ref|NM_012297.2| Homo sapiens Ras-GTPase activating protein SH3
domain-binding protein 2 (KIAA0660), mRNA
Length = 4210

Identities = 599/633 (94%), Gaps = 15/633 (2%)
 Strand = Plus / Minus

```
Query: 33   ggctcaggttcaggttcatgagaggattcttccaaaggctcctctatgccattagtcaca 92
            ||||||||||||||||||||||||||||||||||||||||||||||||||||||||||||
Sbjct: 719  ggctcaggttcaggttcatgagaggattcttccaaaggctcctctatgccattagtcaca 660

Query: 93   ggggtgagcttcatagtaaccactgttagcatttcttgcacaggttcaggagatggttg 152
            ||| ||||||||||||||||||||||||||||||||||||||||||||||||||||||||
Sbjct: 659  ggg-tgagcttcatagtaaccactgttagcatttcttgcacaggttcaggagatggttg 601

Query: 153  tctttcttcttgttcctcttctactttatcttctgattcttcatcaagttcaggctcaga 212
            |||||||||||||||||||||||||| ||||||||||||||||||||||||||||||||
Sbjct: 600  tctttcttcttgttcctcttctacttcatcttctgattcttcatcaagttcaggctcaga 541

Query: 213  atcaccaaacacttcatcttcataacgaaacatatcattgtgaacattaaatttatttgg 272
            |||||||||||||||||||||||||||||||||||||||||||||||| |||||||||||
Sbjct: 540  atcaccaaacacttcatcttcataacgaaacatatcattgtgaacataaaatttatttgg 481

Query: 273  aacagatccttcaggagcccgaaccaaggtttgcctaaactttctttctggttgtccac 332
            |||||||||||||||||| ||||  |||||||||| ||||| ||||||||||||||||||
Sbjct: 480  aacagatccttcaggagccagaacaaaggtttgcataaac-tttctttctggttgtccac 422

Query: 333  tgtttgacagcaaacccatgacctggacaactactccctcactcacggttgccttgagac 392
            |||| |||||||||||||||||||||||||||||||| ||||||||  |||||| |  ||
Sbjct: 421  tgttagacagcaaacccatgacctggacaactactccatcactcaaggttgcat---gag 365

Query: 393  tttccccttgacgaatatttagtatgactttcactgaagtttcagagataatactttgtg 452
            ||| | |||||||||  |||||||||||| |||||||| |||||||||||||||||||||
Sbjct: 364  catccacatgacgaat-tttagtatgacattcactgaag-ttcagagataatactttgtg 307

Query: 453  gtgtatatcatttggccataaacagcttcctggggctttccactagcatctactccacc 512
            ||||||||||||||||||||||||||||||||||||||||||||||||||||||||||||
Sbjct: 306  gtgtatatcatttggccataaacagcttcctggggctttccactagcatctactccacc 247

Query: 513  atgaacataggaagaattcctgccaataaaaacctggtgttaaatattcccggagcttta 572
            |||||||||||||||||||||||||  ||||||| ||| |||||||  |||||||||||
Sbjct: 246  atgaacataggaagaattcctgcca--taaaacct-gtg-taaatatt-ccggagcttta 192

Query: 573  ttcagcaaggtataatatttgcctcacaaaactcccgccttacaagcagcggactgggct 632
            |||||||| ||||||| ||||||||| ||||||||||| |||||||||||||||||||||
Sbjct: 191  ttcagcaaagtataata-ttgcctcac-aaactcccgccctacaagcagcggactgggct 134

Query: 633  tctccataaccatttccttgctgc-caatgtca 664
            |||||||||||||||| |||||||  ||||||
Sbjct: 133  tctccataaccatttctttgctgcacaatgtca 101
```

Figure 17O

Homo sapiens RNA-binding protein G3BP-2
Protein accession number AAH11731
Nucleic acid accession numbers: BC011731, AF145284, AF053535

>gi|15079866|gb|BC011731.1|BC011731 Homo sapiens, Similar to ras-GTPase-
activating protein (GAP<120>), SH3-domain-binding protein 2, clone MGC:19504
IMAGE:4337457, mRNA, complete cds
Length = 2634

Identities = 254/263 (96%), Gaps = 6/263 (2%)
 Strand = Plus / Plus

```
Query: 19   gtcgcacgtcgcagcgcctggcgcccgggaaaaggtggttgtgaggcagacgaactcgcg 78
            |||||||||||||||||||||||||||||||| |||||||||||||||||||||||||||
Sbjct: 14   gtcgcacgtcgcagcgcctggcgcccgggaagaggtggttgtgaggcagacgaactcgcg 73

Query: 79   gctctccggcttccgaggcttccgagattgtcggaggaaggggggcggcgagacaataaga 138
            |||||||||||||||||||||||||||| ||||||||||||||||||||| |||||||
Sbjct: 74   gctctccggcttccgaggcttccgag-ttgtcggaggaaggggggcggcgag-caataaga 131

Query: 139  acccgccgcacccggtcctcagcgactcttctgacctccgcgcgacgtacccgccgccgc 198
            ||||||||||||||||||||||||||||||||||||||||||||||||||||||||||||
Sbjct: 132  acccgccgcacccggtcctcagcgactcttctgacctccgcgcgacgtacccgccgccgc 191

Query: 199  cgtt-gctggagcatttgacattgtgcagc-aagaaatggtt-tggagaagcccagtccg 255
            |||| |||||||||||||||||||||||| |||||||||||| |||||||||||||||||
Sbjct: 192  cgttggctggagcatttgacattgtgcagcaaagaaatggttatggagaagcccagtccg 251

Query: 256  ct-cttgtaangcgggagtttgt 277
            || |||||| ||||||||||||
Sbjct: 252  ctgcttgtagggcgggagtttgt 274
```

Figure 17P

Delta7-sterol reductase
Protein accession number NP_001351
Nucleic acid accession numbers: AP002387.4|, AF110060, NM_001360.1|

>gi|4503320|ref|NM_001360.1| Homo sapiens 7-dehydrocholesterol reductase (DHCR7), mRNA
Length = 2597

Identities = 142/144 (98%), Gaps = 1/144 (0%)
 Strand = Plus / Plus

```
Query: 263 ctctggtttgcaaacgctcatctcctgtcctggttctcgcccaccatcatcttcgacaac 322
           ||||||||||||||||||||||||||||||||||||||||||||||||||||||||||||
Sbjct: 663 ctctggtttgcaaacgctcatctcctgtcctggttctcgcccaccatcatcttcgacaac 722

Query: 323 tggatcccactgctgtggtgcgccaacatccttggctatgccgtctccaccgttcgccat 382
           |||||||||||||||||||||||||||||||||||||||||||||||||| ||||||||
Sbjct: 723 tggatcccactgctgtggtgcgccaacatccttggctatgccatctccacc-ttcgccat 781

Query: 383 ggtcgagggctacttcttcccccac 406
           |||| ||||||||||||||||||||
Sbjct: 782 ggtcaagggctacttcttcccccac 805
```

Figure 17Q

Ubiquitin conjugating enzyme E2M
Protein accession number AAH08963
Nucleic acid accession numbers: BC015662.1|, BC015789, BC008963, BC008832, BC007657, BC004924, HUMHMGIY, HSHMGY, HSHMGI, HUMHMGYD >gi|18182853|gb|BC015662.1| Homo sapiens, clone IMAGE:4844539, mRNA
Length = 1088

Identities = 158/159 (99%), Gaps = 1/159 (0%)
 Strand = Plus / Minus

```
Query:  43 ggccccaggattcccccagccaaactgtctttgtcaccacgtggggctcacttttcatc 102
           |||||||||||||||||||||||||||||||||||||||||||||||||||||||||||
Sbjct: 865 ggccccaggattcccccagccaaactgtctttgtcaccacgtggggctcacttttcatc 806

Query: 103 cttccccaacttccctagtccccgtacta-gttggacagccccttcggctacaggaagg 161
           |||||||||||||||||||||||||||||  |||||||||||||||||||||||||||||
Sbjct: 805 cttccccaacttccctagtccccgtactaggttggacagccccttcggctacaggaagg 746

Query: 162 caggaggggtgagtcccctactccctcttcactgtggcc 200
           |||||||||||||||||||||||||||||||||||||||
Sbjct: 745 caggaggggtgagtcccctactccctcttcactgtggcc 707
```

MODULATORS OF ANGIOGENESIS AND TUMORIGENESIS

CROSS-REFERENCES TO RELATED APPLICATIONS

The present application claims the benefit of U.S. Ser. No. 60/545,981, filed Feb. 17, 2004, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of angiogenesis and tumorigenesis. The invention further relates to methods for identifying and using agents, including small organic molecules, antibodies, peptides, cyclic peptides, nucleic acids, antisense nucleic acids, RNAi, and ribozymes, that modulate angiogenesis and tumorigenesis via modulation of endothelial cell haptotaxis; as well as to the use of expression profiles and compositions in diagnosis and therapy of angiogenesis and cancer.

BACKGROUND OF THE INVENTION

The migration of activated endothelial cells through a vitronectin-rich provisional matrix is critical to the formation of new blood vessels during angiogenesis and is dependent on adhesion receptors containing alphav integrins (such as alphavbeta3 which binds to vitronectin). Peptide and antibody inhibitors of alphavbeta3 integrin inhibit tumor growth in vivo.

Angiogenesis is typically limited in a normal adult to the placenta, ovary, endometrium and sites of wound healing. However, angiogenesis, or its absence, plays an important role in the maintenance of a variety of pathological states. Some of these states are characterized by neovascularization, e.g., cancer and tumorigenesis, e.g., fertility, endometriosis, diabetic retinopathy, glaucoma, glomerulonephritis, and age related macular degeneration. Others, e.g., stroke, infertility, heart disease, e.g., restenosis, ulcers, and scleroderma, are diseases of angiogenic insufficiency. Therefore, there is a need to identify nucleic acids encoding proteins involved in the regulation of angiogenesis and tumorigenesis, to identify, e.g., modulators of angiogenesis, as well as new therapeutic and diagnostic applications.

SUMMARY OF THE INVENTION

Novel targets for anti-angiogenic and anti-tumorigenic therapy have been identified using a functional genetic screen based on endothelial cell haptotaxis. The novel targets are: phosphatidylinositol 4-kinase beta, phosphatidylinositol 4-kinase type II, MAP/ERK kinase kinase 3, SHIP2 inositol phosphatase, delta7-sterol reductase, protein geranylgeranyltransferase type I, glucosamine-6-sulfatase, carbohydrate sulfotransferase 1 (CHST1), heat shock protein 105 kDa beta, UCH-L1 ubiquitin carboxyl-terminal hydrolase, ubiquitin-conjugating enzyme E2M, equilibrative nucleoside transporter 1 (hENT1/SLC29A1), novel LIV-1-related 6 TM protein (6TM ZIP zinc transporter domain), frizzled-4, stathmin1/oncoprotein 1 adaptor, and *Homo sapiens* RNA-binding protein G3BP-2.

Inhibition or activation of these targets (by small molecule inhibitors; protein, antibody and peptide therapeutics; RNAi; antisense; gene therapy etc.) have therapeutic value in modulating angiogenesis and tumorigenesis, e.g., breast, lung, colon, ovarian, liver, kidney, pancreatic, thyroid, stomach, bladder, and prostate cancer, basal cell carcinoma, melanoma, lymphomas (e.g., Hodgkins and non-Hodgkins), leukemias, e.g., myeloid leukemia (CML and AML), endometriosis, diabetic retinopathy, glaucoma, glomerulonephritis, age related macular degeneration, as well as, e.g., stroke, infertility, fertility, heart disease, e.g., restenosis, ulcers, and scleroderma.

The present invention therefore provides nucleic acids encoding proteins involved in modulation of vitronectin induced endothelial cell haptotaxis and modulation of angiogenesis and tumorigenesis. The invention therefore provides methods of screening for compounds, e.g., small organic molecules, antibodies, nucleic acids, peptides, cyclic peptides, nucleic acids, antisense molecules, RNAi, and ribozymes, that are capable of modulating angiogenesis or tumorigenesis, e.g., either activating or inhibiting angiogenesis or tumorigenesis. Therapeutic and diagnostic methods and reagents are also provided.

In one aspect, the present invention provides a method for identifying a compound that modulates angiogenesis and tumorigenesis, the method comprising the steps of: (i) contacting the compound with an angiogenesis or tumorigenesis modulating polypeptide or fragment thereof selected from the group consisting of phosphatidylinositol 4-kinase beta, phosphatidylinositol 4-kinase type II, MAP/ERK kinase kinase 3, SHIP2 inositol phosphatase, delta7-sterol reductase, protein geranylgeranyltransferase type I, glucosamine-6-sulfatase, carbohydrate sulfotransferase 1 (CHST1), heat shock protein 105 kDa beta, UCH-L1 ubiquitin carboxyl-terminal hydrolase, ubiquitin-conjugating enzyme E2M, equilibrative nucleoside transporter 1 (hENT1/SLC29A1), novel LIV-1-related 6 TM protein (6TM ZIP zinc transporter domain), frizzled-4, stathmin1/oncoprotein 1 adaptor, and *Homo sapiens* RNA-binding protein G3BP-2, the polypeptide encoded by a nucleic acid that hybridizes under stringent conditions to a reference nucleic acid encoding the polypeptide; and (ii) determining the functional effect of the compound upon the polypeptide.

In one embodiment, the functional effect is determined in vitro. In another embodiment, the functional effect is a physical effect. In another embodiment, the functional effect is determined by measuring ligand binding to the polypeptide. In another embodiment, the functional effect is a chemical effect.

In one embodiment, the polypeptide is expressed in a eukaryotic host cell. In another embodiment, the functional effect is a physical effect. In another embodiment, the functional effect is determined by measuring ligand binding to the polypeptide. In another embodiment, the functional effect is a chemical or phenotypic effect. In another embodiment, the polypeptide is expressed in a eukaryotic host cell, e.g., an endothelial cell. In another embodiment, the functional effect is determined by measuring αvβ3 expression, haptotaxis, tumor cell proliferation, or tumor growth in vivo.

In one embodiment, modulation is inhibition of angiogenesis or tumorigenesis.

In one embodiment, the polypeptide is recombinant.

In one embodiment, the compound is an antibody, a peptide, an antisense molecule, a RNAi molecule, or a small organic molecule.

In another aspect, the present invention provides a method for identifying a compound that modulates tumorigenesis or angiogenesis, the method comprising the steps of (i) contacting the compound with an angiogenesis or tumorigenesis modulating polypeptide or fragment or inactive variant thereof selected from the group consisting of phosphatidylinositol 4-kinase beta, phosphatidylinositol 4-kinase type II, MAP/ERK kinase kinase 3, SHIP2 inositol phosphatase, delta7-sterol reductase, protein geranylgeranyltransferase type I, glucosamine-6-sulfatase, carbohydrate sulfotransferase 1 (CHST1), heat shock protein 105 kDa beta, UCH-L1 ubiquitin carboxyl-terminal hydrolase, ubiquitin-conjugating enzyme E2M, equilibrative nucleoside transporter 1 (hENT1/SLC29A1), novel LIV-1-related 6 TM protein (6TM ZIP zinc transporter domain), frizzled-4, stathmin1/oncoprotein 1 adaptor, and Homo sapiens RNA-binding protein G3BP-2, (ii) determining the physical effect of the compound upon the polypeptide or fragment thereof or inactive variant thereof; and (iii) determining the chemical or phenotypic effect of the compound upon a cell comprising the polypeptide or fragment thereof or inactive variant thereof, thereby identifying a compound that modulates tumorigenesis or angiogenesis.

In another aspect, the present invention provides a method of modulating angiogenesis or tumorigenesis in a subject, the method comprising the step of administering to the subject a therapeutically effective amount of a compound identified using the methods described herein.

In one embodiment, the subject is a human.

In one embodiment, the compound is an antibody, an antisense molecule, a peptide, or an RNAi molecule, or a small organic molecule.

In one embodiment, the compound inhibits angiogenesis or tumorigenesis.

BRIEF DESCRIPTION OF THE DRAWINGS

FIG. 3 shows selected cDNAs identified using a haptotaxis assay.

FIG. 5 describes phosphatidyliositol 4'-kinase type II α.

FIG. 6 describes delta7-dehydrocholesterol reductase.

FIG. 7 describes HSP105.

FIG. 9 describes HENT1.

FIG. 10 describes novel 6 TM zinc transporter.

FIG. 16 shows a sponge angiogenesis/xenograft model.

FIG. 17 shows exemplary nucleic acid and protein accession numbers for the proteins corresponding to the cDNAs identified in the haptotaxis assay, as well as the sequences the cDNAs identified in the screening assay. The orientation of the cDNAs identified in the screen is provided in FIG. 3. FIG. 17A illustrates an alignment between a cDNA sequence identified in a haptotaxis assay (SEQ ID NO: 1; Query) and phosphatidylinositol 4-kinase beta cDNA (SEQ ID NO: 2; Subject). FIG. 17B illustrates an alignment between a cDNA sequence identified in a haptotaxis assay (SEQ ID NO: 3; Query) and phosphatidylinositol 4-kinase type II cDNA (SEQ ID NO: 4; Subject). FIG. 17C illustrates an alignment between a cDNA sequence identified in a haptotaxis assay (SEQ ID NO: 5; Query) and MAP/ERK kinase kinase 3 cDNA (SEQ ID NO: 6; Subject). FIG. 17D illustrates an alignment between a cDNA sequence identified in a haptotaxis assay (SEQ ID NO: 7; Query) and SHIP2 inositol phosphatase cDNA (SEQ ID NO: 8; Subject). FIG. 17E illustrates an alignment between a cDNA sequence identified in a haptotaxis assay (SEQ ID NO: 9; Query) and protein geranylgeranyltransferase type I cDNA (SEQ ID NO: 33; Subject). FIG. 17F illustrates an alignment between a cDNA sequence identified in a haptotaxis assay (SEQ ID NO: 10; Query) and glucosamine-6-sulfatase cDNA (SEQ ID NO: 11; Subject). FIG. 17G illustrates an alignment between a cDNA sequence identified in a haptotaxis assay (SEQ ID NO: 12; Query) and carbohydrate sulfotransferase 1 cDNA (SEQ ID NO: 13; Subject). FIG. 17H illustrates an alignment between a cDNA sequence identified in a haptotaxis assay (SEQ ID NO: 14; Query) and heat shock protein 105 kDa beta cDNA (SEQ ID NO: 15; Subject). FIG. 17I illustrates an alignment between a cDNA sequence identified in a haptotaxis assay (SEQ ID NO: 16; Query) and UCH-L1 ubiquitin carboxyl terminal hydrolase cDNA (SEQ ID NO: 17; Subject). F*igure* 17J illustrates an alignment between a cDNA sequence identified in a haptotaxis assay (SEQ ID NO: 18; Query) and equilibrative nucleoside transporter 1 cDNA (SEQ ID NO: 19; Subject). FIG. 17K illustrates an alignment between a cDNA sequence identified in a haptotaxis assay (SEQ ID NO: 20; Query) and novel LIV-1-related 6TM protein cDNA (SEQ ID NO: 21; Subject). FIG. 17L illustrates an alignment between a cDNA sequence identified in a haptotaxis assay (SEQ ID NO: 22; Query) and Frizzled 4 cDNA (SEQ ID NO: 34; Subject). FIG. 17M illustrates an alignment between a cDNA sequence identified in a haptotaxis assay (SEQ ID NO: 23; Query) and stathmin 1 cDNA (SEQ ID NO: 35; Subject). FIG. 17N illustrates an alignment between a cDNA sequence identified in a haptotaxis assay (SEQ ID NO: 24; Query) and RNA-binding protein G3BP2 cDNA (SEQ ID NO: 25; Subject). FIG. 17O illustrates an alignment between a cDNA sequence identified in a haptotaxis assay (SEQ ID NO: 26; Query) and RNA-binding protein G3BP-2 cDNA (SEQ ID NO: 27; Subject). FIG. 17P illustrates an alignment between a cDNA sequence identified in a haptotaxis assay (SEQ ID NO: 28; Query) and delta7-sterol reductase cDNA (SEQ ID NO: 29; Subject). FIG. 17Q illustrates an alignment between a cDNA sequence identified in a haptotaxis assay (SEQ ID NO: 30; Query) and ubiquitin conjugating enzyme E2M cDNA (SEQ ID NO: 31; Subject).

DETAILED DESCRIPTION OF THE INVENTION

Introduction

Figure 1:
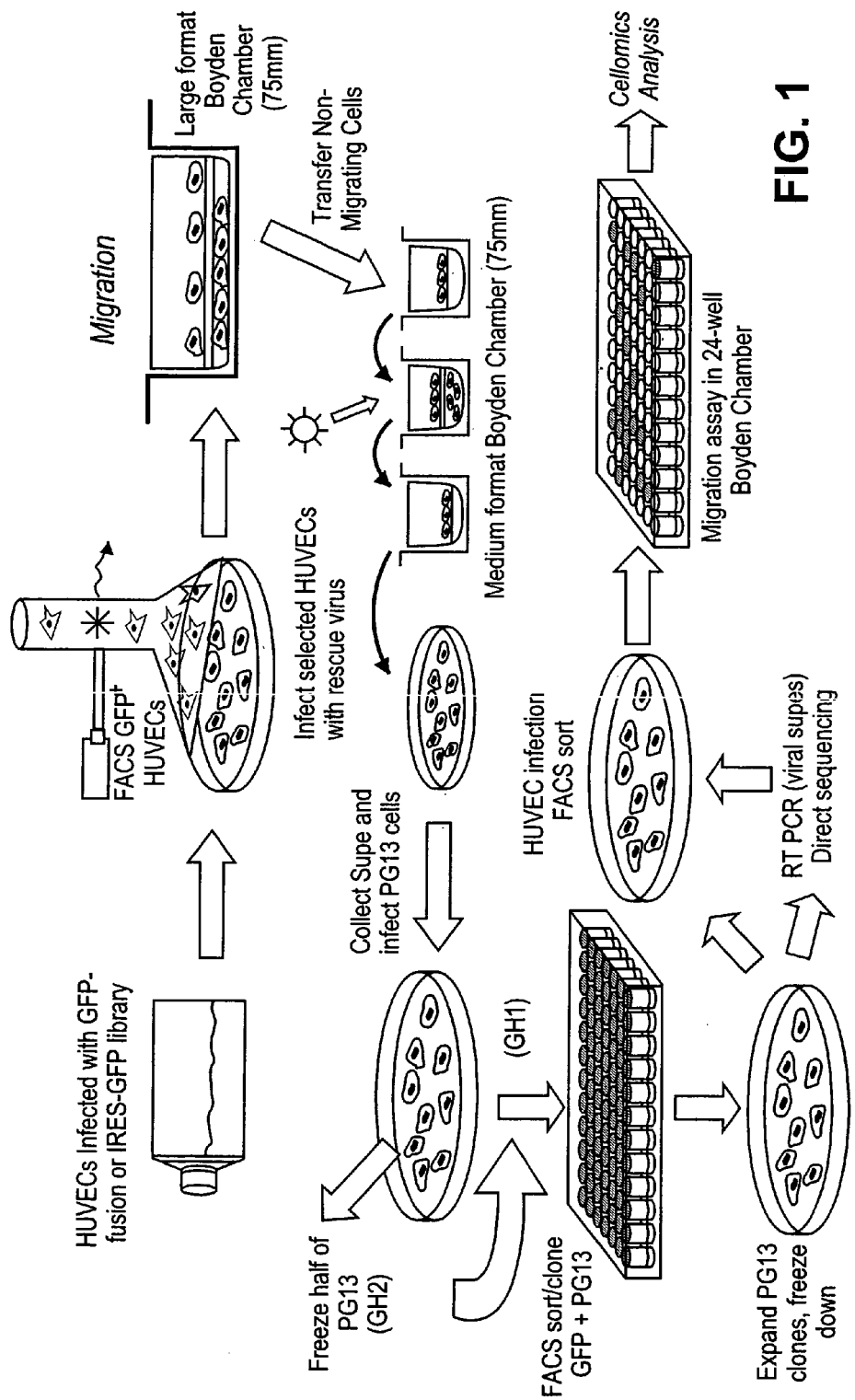
FIG. 1 shows a screening protocol for haptotactic migration inhibitors.

We have used a functional genetic screening strategy to identify proteins involved in regulating endothelial cell migration on specific matrix components, e.g. vitronectin. Using a retroviral-based system, we have stably expressed complex libraries of various types of genetic elements (e.g. cDNAs and GFP-fusions) in human primary endothelial cells (e.g. HUVECs). Starting with early passage primary endothelial cells representing an "angiogenic state" (i.e., proliferative, highly motile), single cells that have switched to a more differentiated "angiostatic state" (i.e., quiescent, reduced motility) can be identified. In order to focus on the migration step of the angiogenic cycle, conditions were established which allowed highly efficient migration of HUVEC cells along a haptotactic gradient of specific matrix proteins (e.g. vitronectin/fibronectin) in a Boyden chamber assay. Large populations of HUVEC cells were then infected with a GFP-fused cDNA library and selected for impaired haptotaxis. Additional assays for proteins involved in angiogenesis and tumorigenesis include a VEGFR2 assay, a HUVEC/smooth muscle cell co-culture assay for endothelial tube formation, chemo-invasion assays, and tumor cell proliferation assays. Finally, human/mouse tumor xenograft assays, mouse sponge angiogenesis and tumorigenesis assays (sponge with human ECs ±human tumor cells in SCID mice), a collagen-antibody induced arthritis model for RA, and retinal neovascularization assays can be used to identify angiogenesis and tumorigenesis proteins in vivo and to assay for modulators of such proteins.

The angiogenesis and tumorigenesis proteins identified using the haptotaxis assay described herein, e.g., phosphatidylinositol 4-kinase beta, phosphatidylinositol 4-kinase type II, MAP/ERK kinase kinase 3, SHIP2 inositol phosphatase, delta7-sterol reductase, protein geranylgeranyltransferase type I, glucosamine-6-sulfatase, carbohydrate sulfotransferase 1 (CHST1), heat shock protein 105 kDa beta, UCH-L1 ubiquitin carboxyl-terminal hydrolase, ubiquitin-conjugating enzyme E2M, equilibrative nucleoside transporter 1 (hENT1/SLC29A1), novel LIV-1-related 6 TM protein (6TM ZIP zinc transporter domain), frizzled-4, stathmin1/oncoprotein 1 adaptor, and *Homo sapiens* RNA-binding protein G3BP-2, therefore represent targets for the development of angiogenic drugs, preferably anti-angiogenic drugs, e.g., anti-angiogenic drugs for treatment of neovascularization, e.g., cancer, diabetic retinopathy, endometriosis, glomerulonephritis, restenosis, glaucoma, rheumatoid arthritis, and age related macular degeneration, or angiogenic drugs for treatment of angiogenic insufficiency, e.g., stroke, infertility, fertility, heart disease, ulcers, and scleroderma.

Modulators include small organic molecules, nucleic acids, peptides, cyclic peptides, antibodies, antisense molecules, RNAi molecules, and ribozymes. The nucleic acids and proteins of the invention are also useful for diagnostic applications, using, e.g., nucleic acid probes, oligonucleotides, and antibodies. These polypeptides are also involved in tumorigenesis and cellular proliferation, and are useful for the development of therapeutic molecules to treat diseases associated with angiogenesis, tumorigenesis, and cellular proliferation. Furthermore, the polypeptides described herein and the nucleic acids encoding them are useful for diagnostic assays for diseases associated with angiogenesis, tumorigenesis, and cellular proliferation.

Definitions

By "disorder associated with angiogenesis or tumorigenesis" or "disease associated with angiogenesis or tumorigenesis" herein is meant a disease state which is marked by either an excess or a deficit of vessel development. Angiogenesis and tumorigenesis disorders associated with increased angiogenesis include, but are not limited to, breast, lung, colon, ovarian, liver, kidney, pancreatic, stomach, bladder, thyroid, and prostate cancer, basal cell carcinoma, melanoma, lymphomas, leukemias, e.g., myeloid leukemia (AML, CML), endometriosis, diabetic retinopathy, glaucoma, glomerulonephritis, rheumatoid arthritis, and age related macular degeneration. Pathological states for which it may be desirable to increase angiogenesis include stroke, infertility, fertility, heart disease, ulcers, e.g., restenosis, ulcers, and scleroderma. An increase in angiogenesis may also be desirable in transplantation or for artificial or in vitro growth of organs.

By "disorder associated with cellular proliferation or tumorigenesis" or "disease associated with cellular proliferation or tumorigenesis" herein is meant a disease state which is marked by either an excess or a deficit of cellular proliferation or apoptosis. Such disorders associated with increased cellular proliferation include, but are not limited to, cancer and non-cancerous pathological proliferation.

The terms "angiogenesis and/or tumorigenesis polypeptide" or a nucleic acid encoding an "angiogenesis and/or tumorigenesis polypeptide" refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

The phrase "functional effects" in the context of assays for testing compounds that modulate activity of an angiogenesis and tumorigenesis protein includes the determination of a parameter that is indirectly or directly under the influence of an angiogenesis polypeptide, e.g., a chemical or phenotypic effect such as loss-of angiogenesis or tumorigenesis phenotype represented by a change in expression of a cell surface marker αvβ3 integrin, changes in cellular migration, changes in endothelial tube formation, and changes in tumor growth, or changes in cellular proliferation, especially endothelial cell proliferation; or enzymatic activity; or, e.g., a physical effect such as ligand binding or inhibition of ligand binding. A functional effect therefore includes ligand binding activity, the ability of cells to proliferate, expression in cells undergoing angiogenesis or tumorigenesis, and other characteristics of angiogenic and tumorigenic cells. "Functional effects" include in vitro, in vivo, and ex vivo activities.

By "determining the functional effect" is meant assaying for a compound that increases or decreases a parameter that is indirectly or directly under the influence of an angiogenesis protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the angiogenesis protein; measuring changes in enzymatic activity; the ability to increase or decrease cellular proliferation, apoptosis, cell cycle arrest, measuring changes in cell surface markers, e.g., αvβ3 integrin; and measuring cellular proliferation, particularly endothelial cell proliferation. Determination of the functional effect of a compound on angiogenesis or tumorigenesis can also be performed using assays known to those of skill in the art such as endothelial cell tube formation assays; haptotaxis assays; the chick CAM assay; the mouse corneal assay; VEGF receptor assays, co-culture tube formation assays, and assays that assess vascularization of an implanted tumor. Tumorigenesis can be measured using in vivo mouse models such as a xenograft model. The functional effects can be evaluated by many means known to those skilled in the art, e.g., microscopy for quantitative or qualitative measures of alterations in morphological features, e.g., tube or blood vessel formation, measurement of changes in RNA or protein levels for angiogenesis-associated sequences, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of angiogenesis and tumorigenesis polynucleotide and polypeptide sequences are used to refer to activating, inhibitory, or modulating molecules identified using in vitro and in vivo assays of angiogenesis and tumorigenesis polynucleotide and polypeptide sequences. Inhibitors are compounds that, e.g., bind to, partially or totally block activity, decrease, prevent, delay activation, inactivate, desensitize, or down regulate the activity or expression of angiogenesis and tumorigenesis proteins, e.g., antagonists. "Activators" are compounds that increase, open, activate, facilitate, enhance activation, sensitize, agonize, or up regulate angiogenesis and tumorigenesis protein activity, agonists. Inhibitors, activators, or modulators also include genetically modified versions of angiogenesis and tumorigenesis proteins, e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing angiogenesis or tumorigenesis protein in vitro, in cells, or cell extracts, applying putative modulator compounds, and then determining the functional effects on activity, as described above.

Samples or assays comprising angiogenesis or tumorigenesis proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of an angiogenesis or tumorigenesis protein is achieved when the activity value relative to the control is about 80%, preferably 50%, more preferably 25-0%. Activation of an angiogenesis or tumorigenesis protein is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate angiogenesis and tumorigenesis. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., SEQ ID NO: 1 or 2), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypepfide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., ligand binding domains, etc. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies, polymorphic variants, alleles, orthologs, and conservatively modified variants, or splice variants, or portions thereof, can be selected to obtain only those polyclonal antibodies that are specifically immunoreactive with angiogenesis proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Assays for Proteins that Modulate Angiogenesis, Tumorigenesis, and Cellular Proliferation High throughput functional genomics assays can be used to identify modulators of angiogenesis and tumorigenesis. Such assays can monitor changes in cell migration or haptotaxis, cell surface marker expression, $\alpha v \beta 3$ integrin production, proliferation, and differentiation using either cell lines or primary cells. Typically, early passage or primary endothelial cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the endothelial cells is then monitored, using an assay such as cell surface marker expression (e.g., $\alpha v \beta 3$ integrin) or a phenotypic assay for angiogenesis such as migration towards an ECM (extracellular matrix) component (see, e.g., Klemke et al., *J. Cell Biol.* 4:961-972 (1998)) or endothelial cell tube formation assays, as well as other bioassays such as the chick CAM assay, the mouse corneal assay, haptotaxis assays, VEGF-R assays, co-culture tube formation assays, and assays measuring the effect of administering potential modulators on implanted tumors. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tags. In vivo assays for tumor growth, such as mouse xenograft models, can also be used.

Proteins interacting with the peptide or with the protein encoded by the cDNA can be isolated using a yeast two-hybrid system, mammalian two hybrid system, or phage display screen, etc. Targets so identified can be further used as bait in these assays to identify additional members of the angiogenesis pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable endothelial cell lines include human umbilical vein cells (see, e.g., Jaffe et al., *J. Clin. Invest.* 52:2745-2754 (1973)); human adult dermal capillary-derived cells (see, e.g., Davison et al., *In Vitro* 19:937-945 (1983)); human adipose capillary derived cells (see, e.g., Kern et al., *J. Clin Invest.* 71:1822-1829 (1983); bovine aorta (see, e.g., Booyse et al., *Thromb. Diathes. Ahemorrh.* 34:825-839 (1975); and rat brain capillary derived cells (see, e.g., Bowman et al., *In Vitro* 17:353-362 (1981)). For culture of endothelial cell lines, explants, and primary cells, see Freshney et al., *Culture of Animal Cells* ($3^{rd}$ ed. 1994). Suitable angiogenesis cell surface markers include alphavbeta3 integrin (see, e.g., Elicerir & Cheresh, *Cancer J. Sci. Am.* 6 Supp. 3:S245-249 (2000), Maeshima et al., *J. Biol. Chem. (Jun. 8, 2001)).

Cell surface markers such as $\alpha v \beta 3$ can be assayed using fluorescently labeled antibodies and FACS. Cell proliferation can be measured using $^3$H-thymidine or dye inclusion. Angiogenesis or tumorigenesis phenotype is measured by loss of phenotype observation.

cDNA libraries are made from any suitable source, preferably from endothelial cells. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

In one embodiment, target proteins that modulate angiogenesis and/or tumorigenesis are identified a haptotaxis assay. Using a retroviral-based system, stably expressed complex cDNA libraries are expressed in human primary endothelial cells (e.g. HUVECs). Starting with early passage primary endothelial cells representing an "angiogenic state" (i.e., proliferative, highly motile), single cells that have switched to a more differentiated "angiostatic state" (i.e., quiescent, reduced motility) can be identified using the haptotaxis assay. Conditions were established which allowed highly efficient migration of HUVEC cells along a haptotactic gradient of specific matrix proteins (e.g. vitronectin/fibronectin) in a Boyden chamber assay. Large populations of HUVEC cells were then infected with a GFP-fused cDNA library and selected for impaired haptotaxis.

In a another embodiment, target proteins that modulate angiogenesis or tumorigenesis are identified using a high throughput cell based assay (using a microtiter plate format) and FACS screening for $\alpha v \beta 3$ cell surface expression. cDNA libraries are made which include, e.g., sense, antisense, full length, and truncated cDNAs. The cDNAs are cloned into a retroviral vector. Endothelial cells are infected with the library, cultured for a short effector phase and then the cells with reduced αvβ3 surface levels are enriched by antibody staining and magnetic cell sorting. The enriched cell population is then sorted into microtiter plates using fluorescent antibodies and FACS. Resultant cell colonies are analyzed by immunofluorescence for reduced αvβ3 surface levels. Selected colonies are infected with wild type MMLV virus to rescue the proviral vector. The infectious supernatant is used to infect endothelial cells, which are subsequently analyzed for αvβ3 levels by FACS. The cDNA is isolated and sequenced to determined if it represents a wild type or mutated cDNA, e.g., whether the cDNA represents a negative transdominant mutant. Optionally, a marker such as GFP can be used to select for retrovirally infected cells.

Isolation of Nucleic Acids

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Nucleic acids, polymorphic variants, orthologs, and alleles can be isolated using nucleic acid probes and oligonucleotides under stringent hybridization conditions, by screening libraries. Alternatively, expression libraries can be used to clone angiogenesis proteins, polymorphic variants, orthologs, and alleles by detecting expressed homologs immunologically with antisera or purified antibodies made against human angiogenesis proteins or portions thereof.

To make a cDNA library, one should choose a source that is rich in the desired RNA, e.g., endothelial cells. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffinan, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.,* 72:3961-3965 (1975).

An alternative method of isolating nucleic acids and orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of angiogenesis protein encoding mRNA in physiological samples, for nucleic acid sequencing, or for other purposes. Genes amplified by the PCR reaction can be purified from agarose gels and cloned into an appropriate vector.

Gene expression can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids can be used with high density oligonucleotide array technology (e.g., GeneChip™) to identify angiogenesis protein, orthologs, alleles, conservatively modified variants, and polymorphic variants in this invention. In the case where the homologs being identified are linked to a known disease state, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding an angiogenesis protein, one typically subclones the desired nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence and signals required for efficient polyadenylation of the transcript, ribosome binding sites, and translation termination. Additional elements of the cassette may include enhancers and, if genomic DNA is used as the structural gene, introns with fuictional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

In one embodiment, the vectors of the invention have a regulatable promoter, e.g., tet-regulated systems and the RU-486 system (see, e.g., Gossen & Bujard, *Proc. Nat'l Acad. Sci. USA* 89:5547 (1992); Oligino et al., Gene Ther. 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the protein of choice, which is recovered from the culture using standard techniques identified below.

Purification of Polypeptides

Either naturally occurring or recombinant protein can be purified for use in functional assays. Naturally occurring protein can be purified, e.g., from human tissue. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand, angiogenesis protein can be selectively adsorbed to a purification column and then freed from the column in a relatively pure form. The fused protein is then removed by enzymatic activity. Finally, protein could be purified using immunoaffinity columns.

A. Purification of Protein from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of Angiogenesis or Tumorigenesis Proteins

A. Assays

Modulation of an angiogenesis protein, and corresponding modulation of angiogenesis or tumorigenesis, can be assessed using a variety of in vitro and in vivo assays, including high throughput ligand binding and cell based assays, as described herein. Such assays can be used to test for inhibitors and activators of the angiogenesis protein, and, consequently, inhibitors and activators of angiogenesis. Such modulators of the angiogenesis protein are useful for treating angiogenesis and tumorigenesis disorders. Modulators of the angiogenesis protein are tested using either recombinant or naturally occurring protein, preferably human protein.

Measurement of an angiogenic or tumorigenic or loss-of-angiogenesis or tumorigenesis phenotype on the protein or cell expressing the protein, either recombinant or naturally occurring, can be performed using a variety of assays, in vitro, in vivo, and ex vivo. For example, recombinant or naturally occurring protein can be used in vitro, in a ligand binding or enzymatic function assay. Protein present in a cellular extract can also be used in in vitro assays. Cell- and animal-based in vivo assays can also be used to assay for angiogenesis modulators. Any suitable physical, chemical, or phenotypic change that affects activity or binding can be used to assess the influence of a test compound on the polypeptide of this invention. When the functional effects are determined using intact cells or animals, one can also measure a variety of effects such as, in the case of angiogenesis associated with tumors, tumor growth, neovascularization, endothelial tube formation, cell surface markers such as $\alpha v\beta 3$, hormone release, transcriptional changes to both known and uncharacterized genetic markers (e.g., northern blots), changes in cell metabolism such as cell growth or pH changes, and changes in intracellular second messengers such as cGMP. In one embodiment, measurement of $\alpha v\beta 3$ integrin cell surface expression and FACS sorting is used to identify modulators of angiogenesis.

In Vitro Assays

Assays to identify compounds with angiogenesis or tumorigenesis modulating activity, e.g., anti-angiogenic or anti-tumorigenic activity, can be performed in vitro, e.g., binding assays. Purified recombinant or naturally occurring protein can be used in the in vitro methods of the invention. In addition to purified protein, the recombinant or naturally occurring protein can be part of a cellular lysate. As described below, the assay can be either solid state or soluble. Preferably, the protein is bound to a solid support, either covalently or non-covalently. Often, the in vitro assays of the invention are ligand binding or ligand affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or chimera comprising a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, and antibodies. A wide variety of assays can be used to identify angiogenesis-modulator binding, including labeled protein-protein binding assays, electrophoretic mobility shifts, immunoassays, and the like. In some cases, the binding of the candidate modulator is determined through the use of competitive binding assays, where interference with binding of a known ligand is measured in the presence of a potential modulator. Often, either the potential modulator or the known ligand is labeled.

Cell-Based in Vivo Assays

In another embodiment, the protein is expressed in a cell, and functional, e.g., physical and chemical or phenotypic, changes are assayed to identify angiogenesis or tumorigenesis modulators, preferably anti-angiogenesis or anti-tumorigenesis compounds. Cells expressing angiogenesis proteins can also be used in binding assays or enzymatic assays. Any suitable functional effect can be measured, as described herein. For example, cell migration (haptotaxis) assays, ligand binding, cell surface marker expression, cellular proliferation, VEGF-R assays, co-culture assays for tube formation, and are all suitable assays to identify potential modulators using a cell based system. Suitable cells for such cell based assays include both primary endothelial cells and cell lines, as described herein. The protein can be naturally occurring or recombinant.

As described above, in one embodiment, loss-of angiogenesis or tumorigenesis phenotype is measured by contacting endothelial cells comprising an angiogenesis target with a potential modulator. Modulation of angiogenesis or tumorigenesis is identified by screening for changed cellular migration, or by screening for altered cell surface marker expression, e.g., $\alpha v\beta 3$ integrin expression levels, using fluorescent antibodies and FACS sorting.

In another embodiment, cellular proliferation can be measured using $^3$H-thymidine incorporation or dye inclusion.

In another embodiment, cellular polypeptide levels are determined by measuring the level of protein or mRNA. The level of protein or proteins are measured using immunoassays such as western blotting, ELISA and the like with an antibody that selectively binds to the polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, protein expression can be measured using a reporter gene system. Such a system can be devised using an angiogenesis protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

A variety of phenotypic angiogenesis or tumorigenesis assays are known to those of skill in the art. Various models have been employed to evaluate angiogenesis (e.g., Croix et al., *Science* 289:1197-1202 (2000) and Kahn et al., *Amer. J. Pathol.* 156:1887-1900). Assessment of angiogenesis or tumorigenesis in the presence of a potential modulator can be performed using cell-culture-based assays, e.g., endothelial cell tube formation assays and haptotaxis assays, as well as other animal based bioassays such as the chick CAM assay, the mouse corneal assay, and assays measuring the effect of administering potential modulators on implanted tumors.

For determination of cellular proliferation, any suitable functional effect can be measured, as described herein. For example, cellular morphology (e.g., cell volume, nuclear volume, cell perimeter, and nuclear perimeter), ligand binding, kinase activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoescht dye with FACS analysis), $G_0/G_1$ cell cycle arrest, are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), Hela (cervical), PC3 (prostate, p53 mutant), MDA-MB-231 (breast, p53 wild-type). Cancer cell lines can be p53 mutant, p53 null, or express wild type p53.

Animal Models

A number of animal based assays for angiogenesis or tumorigenesis phenotypes are known to those of skill in the art and can be used to assay for modulators of angiogenesis. For example, the chick CAM assay is described by O'Reilly, et al. *Cell* 79: 315-328 (1994). Briefly, 3 day old chicken embryos with intact yolks are separated from the egg and placed in a petri dish. After 3 days of incubation, a methylcellulose disc containing the protein to be tested is applied to the CAM of individual embryos. After about 48 hours of incubation, the embryos and CAMs are observed to determine whether endothelial growth has been inhibited.

The mouse corneal assay involves implanting a growth factor-containing pellet, along with another pellet containing the suspected endothelial growth inhibitor, in the cornea of a mouse and observing the pattern of capillaries that are elaborated in the cornea.

Angiogenesis can also be measured by determining the extent of neovascularization of a tumor. For example, carcinoma cells can be subcutaneously inoculated into athymic or nude mice or SCID mice and tumor growth then monitored. Immunoassays using endothelial cell-specific antibodies are typically used to stain for vascularization of tumor and the number of vessels in the tumor.

As described above, animal models of angiogenesis find use in screening for modulators of angiogenesis and tumorigenesis. Similarly, transgenic animal technology including gene knockout technology, for example as a result of homologous recombination with an appropriate gene targeting vector, or gene overexpression, will result in the absence or increased expression of the protein. The same technology can also be applied to make knock-out cells. When desired, tissue-specific expression or knockout of the protein may be necessary. Transgenic animals generated by such methods find use as animal models of angiogenesis and are additionally useful in screening for modulators of angiogenesis and tumorigenesis.

Knock-out cells and transgenic mice can be made by insertion of a marker gene or other heterologous gene into the endogenous gene site in the mouse genome via homologous recombination. Such mice can also be made by substituting the endogenous gene with a mutated version of the gene, or by mutating the endogenous gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators

The compounds tested as modulators of the angiogenesis protein can be any small organic molecule, or a biological entity, such as a protein, e.g., an antibody or peptide, a sugar, a nucleic acid, e.g., an antisense oligonucleotide, RNAi molecule, or a ribozyme, or a lipid. Alternatively, modulators can be genetically altered versions of an angiogenesis protein. Typically, test compounds will be small organic molecules, peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule, peptide library, or circular peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries and circular peptide libraries (see, e.g., U.S. Pat. No. 5,010,175, U.S. Pat. No. 6,153,380, U.S. Pat. No. 6,365,344, and U.S. Pat. No. 6,455,247, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, MO, ChemStar, Ltd, Moscow, RU, 3D Pharmaceuticals, Exton, PA, Martek Biosciences, Columbia, Md., etc.).

C. Solid State and Soluble High Throughput Assays

In one embodiment the invention provides soluble assays using an angiogenesis protein, or a cell or tissue expressing an angiogenesis protein, either naturally occurring or recombinant. In another embodiment, the invention provides solid phase based in vitro assays in a high throughput format, where the angiogenesis protein is attached to a solid phase substrate. Any one of the assays described herein can be adapted for high throughput screening, e.g., ligand binding, cellular proliferation, cell surface marker flux, e.g., $\alpha v \beta 3$ integrin, etc. In one preferred embodiment, the cell-based system using $\alpha v \beta 3$ integrin modulation and FACS assays is used in a high throughput format for identifying modulators of angiogenesis proteins, and therefore modulators of T cell angiogenesis.

In the high throughput assays of the invention, either soluble or solid state, it is possible to screen up to several thousand different modulators or ligands in a single day. This methodology can be used for angiogenesis proteins in vitro, or for cell-based assays comprising an angiogenesis protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:32). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Antibodies to Angiogenesis and Tumorigenesis Polypeptides

In addition to the detection of gene and gene expression using nucleic acid hybridization technology, one can also use immunoassays to detect proteins of the invention. Such assays are useful for screening for modulators of angiogenesis, as well as for therapeutic and diagnostic applications. Immunoassays can be used to qualitatively or quantitatively analyze angiogenesis protein. A general overview of the applicable technology can be found in Harlow & Lane, *Antibodies: A Laboratory Manual* (1988).

A. Production of Antibodies

Methods of producing polyclonal and monoclonal antibodies that react specifically with the angiogenesis proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of an angiogenesis protein may be used to produce antibodies specifically reactive with protein. For example, recombinant protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-angiogenesis proteins, using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better. Antibodies specific only for a particular ortholog, such as a human ortholog, can also be made, by subtracting out other cross-reacting orthologs from a species such as a non-human mammal. In this manner, antibodies that bind only to a desired protein may be obtained.

Once the specific antibodies against the protein are available, the protein can be detected by a variety of immunoassay methods. In addition, the antibody can be used therapeutically as modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

Protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the protein or antigenic subsequence thereof). The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled protein or a labeled antibody. Alternatively, the labeling agent may be a third moiety, such a secondary antibody, that specifically binds to the antibody/protein complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting protein in samples may be either competitive or noncompetitive. Noncompetitive immunoassays are assays in which the amount of antigen is directly measured. In one preferred "sandwich" assay, for example, the antibodies can be bound directly to a solid substrate on which they are immobilized. These immobilized antibodies then capture protein present in the test sample. Proteins thus immobilized are then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of protein present in the sample is measured indirectly by measuring the amount of a known, added (exogenous) protein displaced (competed away) from an antibody by the unknown protein present in a sample. In one competitive assay, a known amount of protein is added to a sample and the sample is then contacted with an antibody that specifically binds to protein. The amount of exogenous protein bound to the antibody is inversely proportional to the concentration of protein present in the sample. In a particularly preferred embodiment, the antibody is immobilized on a solid substrate. The amount of protein bound to the antibody may be determined either by measuring the amount of protein present in protein/antibody complex, or alternatively by measuring the amount of remaining uncomplexed protein. The amount of protein may be detected by providing a labeled molecule.

A hapten inhibition assay is another preferred competitive assay. In this assay the known protein is immobilized on a solid substrate. A known amount of antibody is added to the sample, and the sample is then contacted with the immobilized protein. The amount of antibody bound to the known immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein can be immobilized to a solid support. Proteins are added to the assay that compete for binding of the antisera to the immobilized antigen. The ability of the added proteins to compete for binding of the antisera to the immobilized protein is compared to the ability of the protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein that is required to inhibit 50% of binding, then the second protein is said to specifically bind to the polyclonal antibodies generated to the immunogen.

Other Assay Formats

Western blot (immunoblot) analysis is used to detect and quantify the presence of protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the protein. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., Amer. Clin. Prod. Rev. 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the protein, or secondary antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Gene Therapy

The present invention provides the nucleic acids of angiogenesis or tumorigenesis associated protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a protein of the present invention, thereby mitigating the effects of absent, partial inactivation, or abnormal expression of the angiogenesis or tumorigenesis gene, particularly as it relates to angiogenesis. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11: 167-175 (1993); Miller, *Nature* 357:455-460 (1992); Van Brunt, *Biotechnology* 6(10): 1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

The nucleic acids of the invention can also be used to make transgenic animals, such as transgenic mice, either by knockout or overexpression. Such animals are useful, e.g., for testing modulators of angiogenesis and tumorigenesis.

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the angiogenesis protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Figure 2:
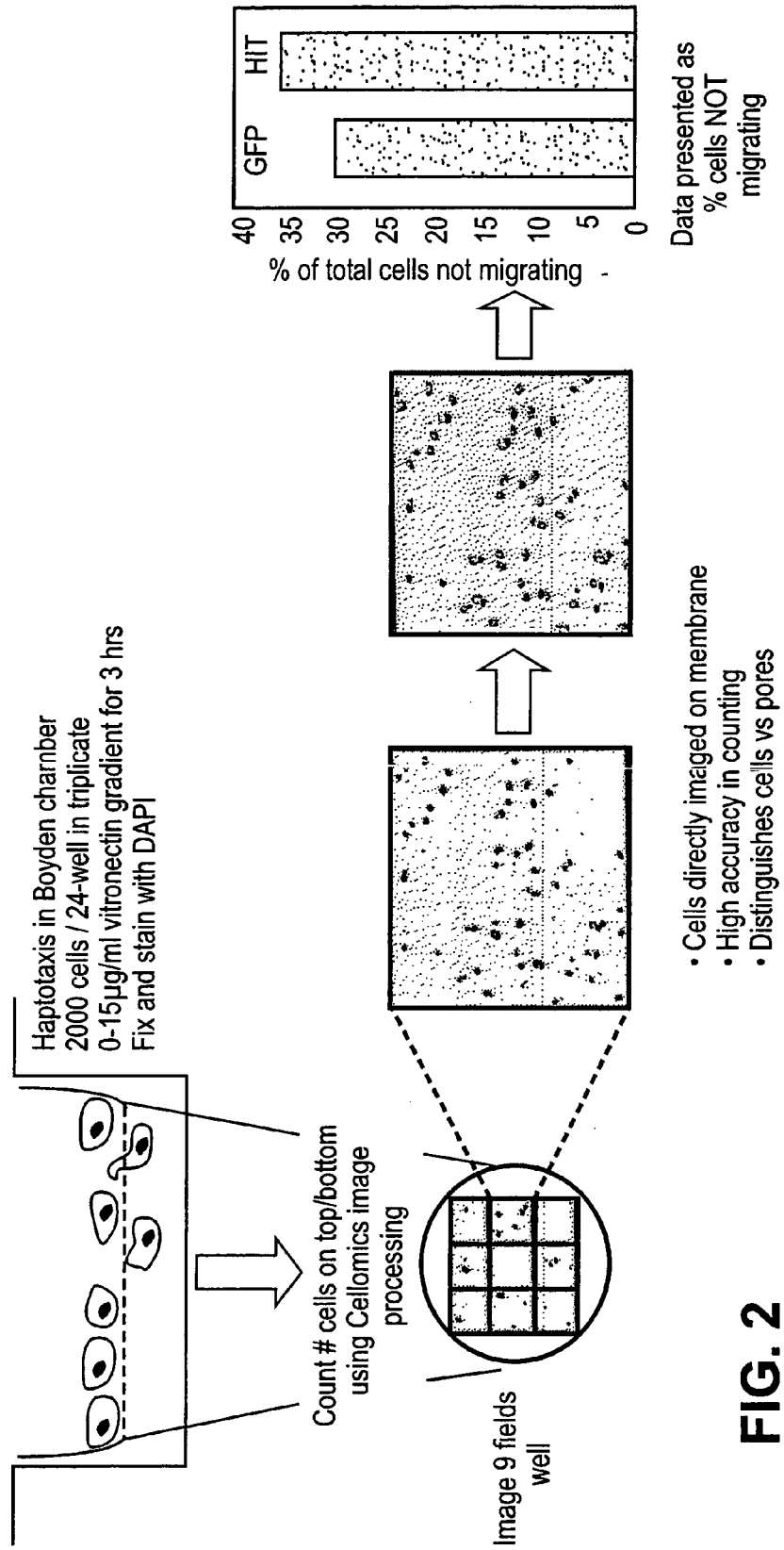
FIG. 2 shows a cellomics haptotaxis assay.
Figure 4:
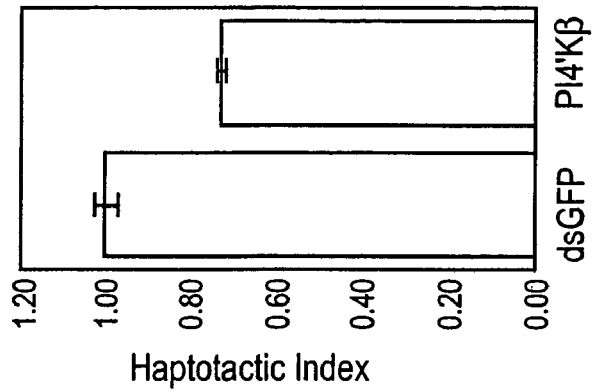
FIG. 4 describes phosphatidylinositol 4'-kinas beta.
Figure 8:
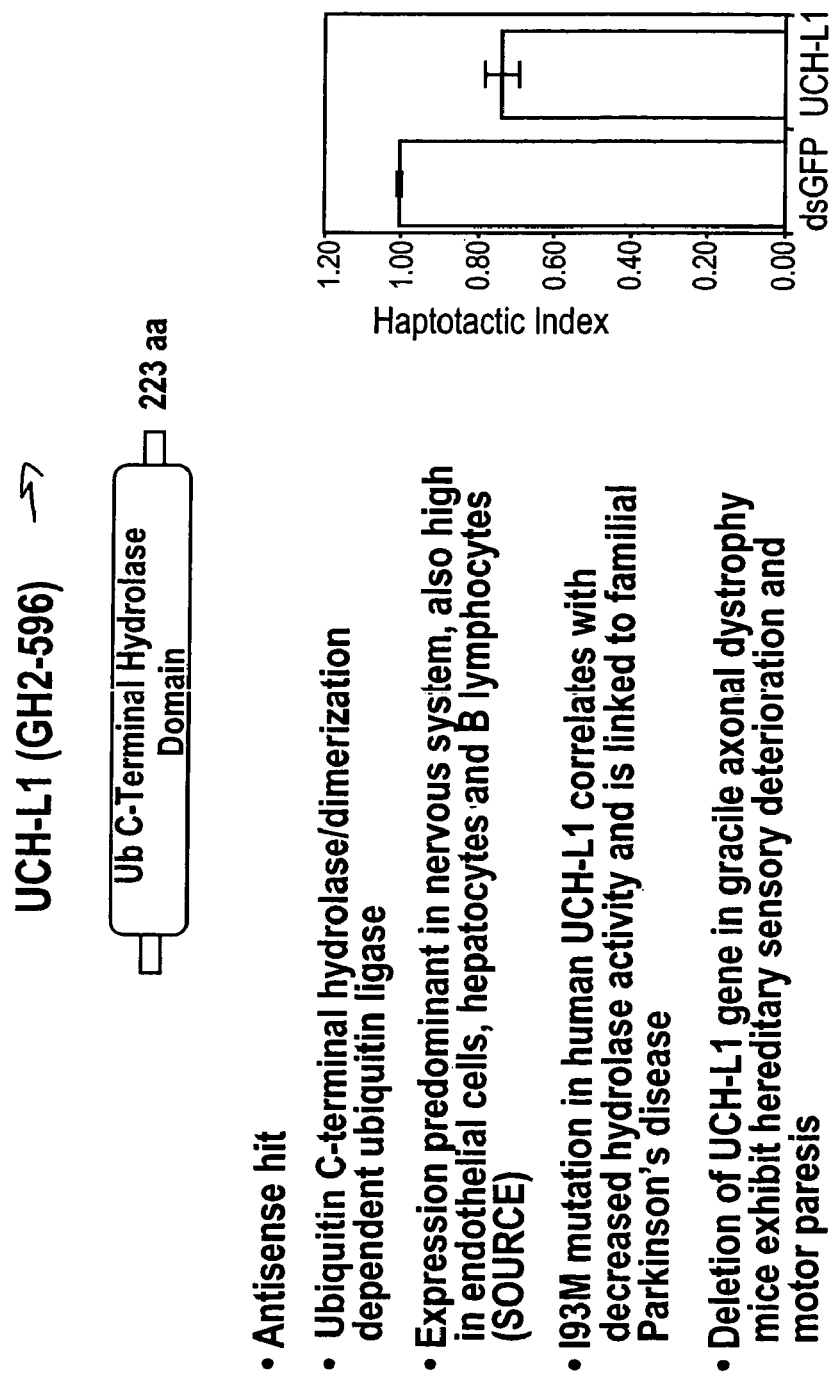
FIG. 8 describes UCH-L1.
Figure 11:
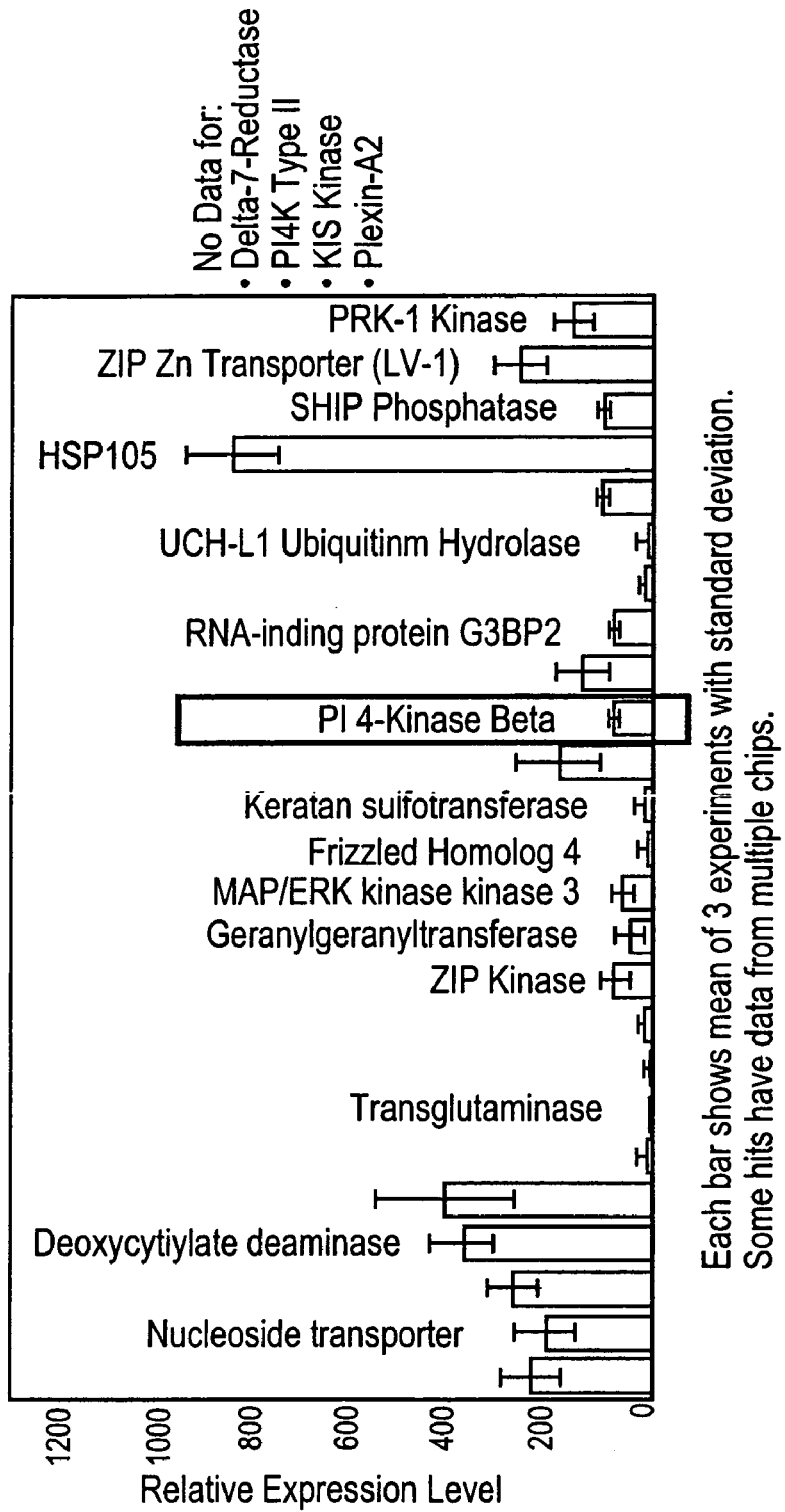
FIG. 11 shows expression of selected haptotaxis screen hits in Jurkat T-cells.
Figure 12:
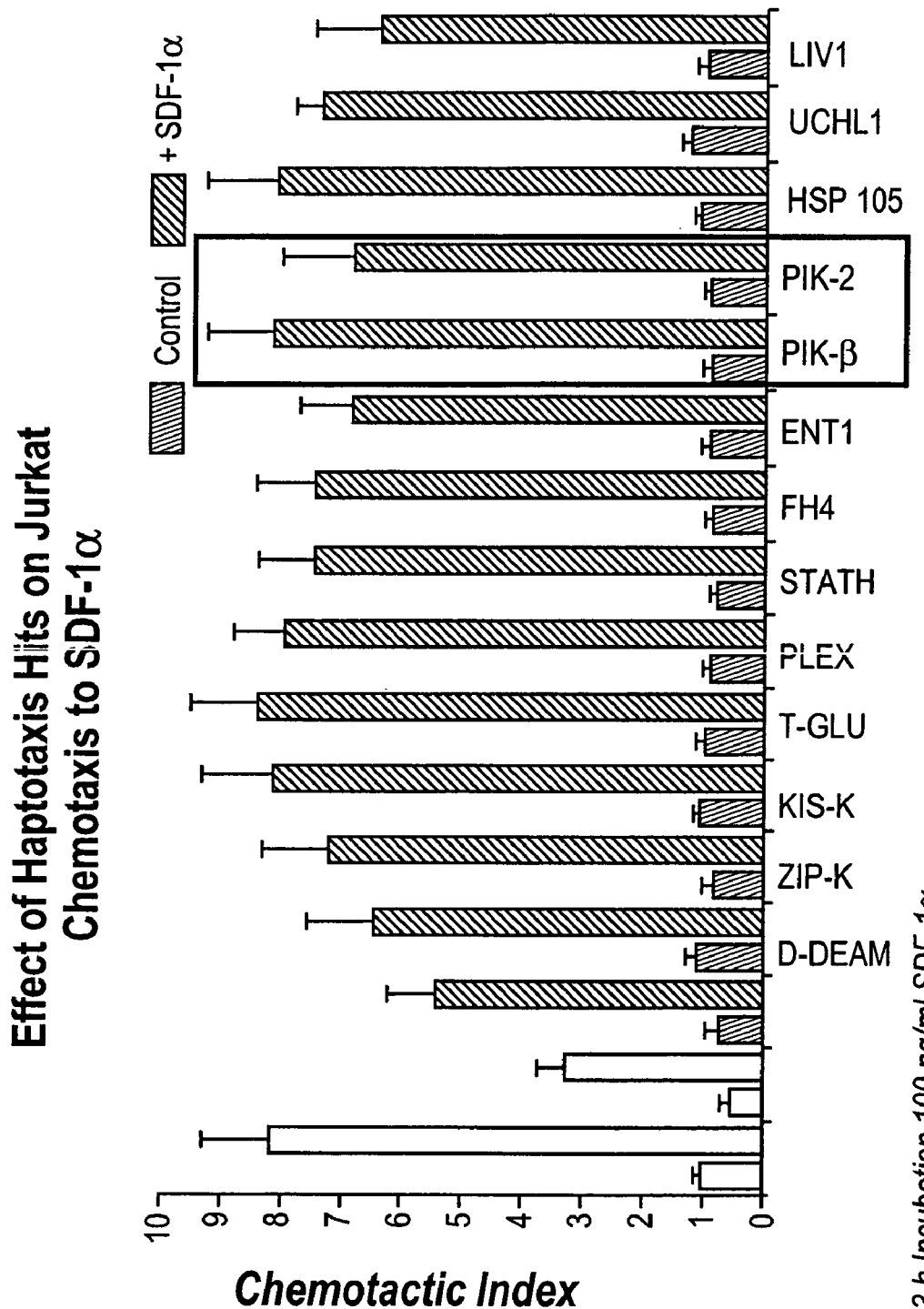
FIG. 12 shows the effect of selected haptotaxis screen hits on Jurkat chemotaxis to SDF-1α.
Figure 13:
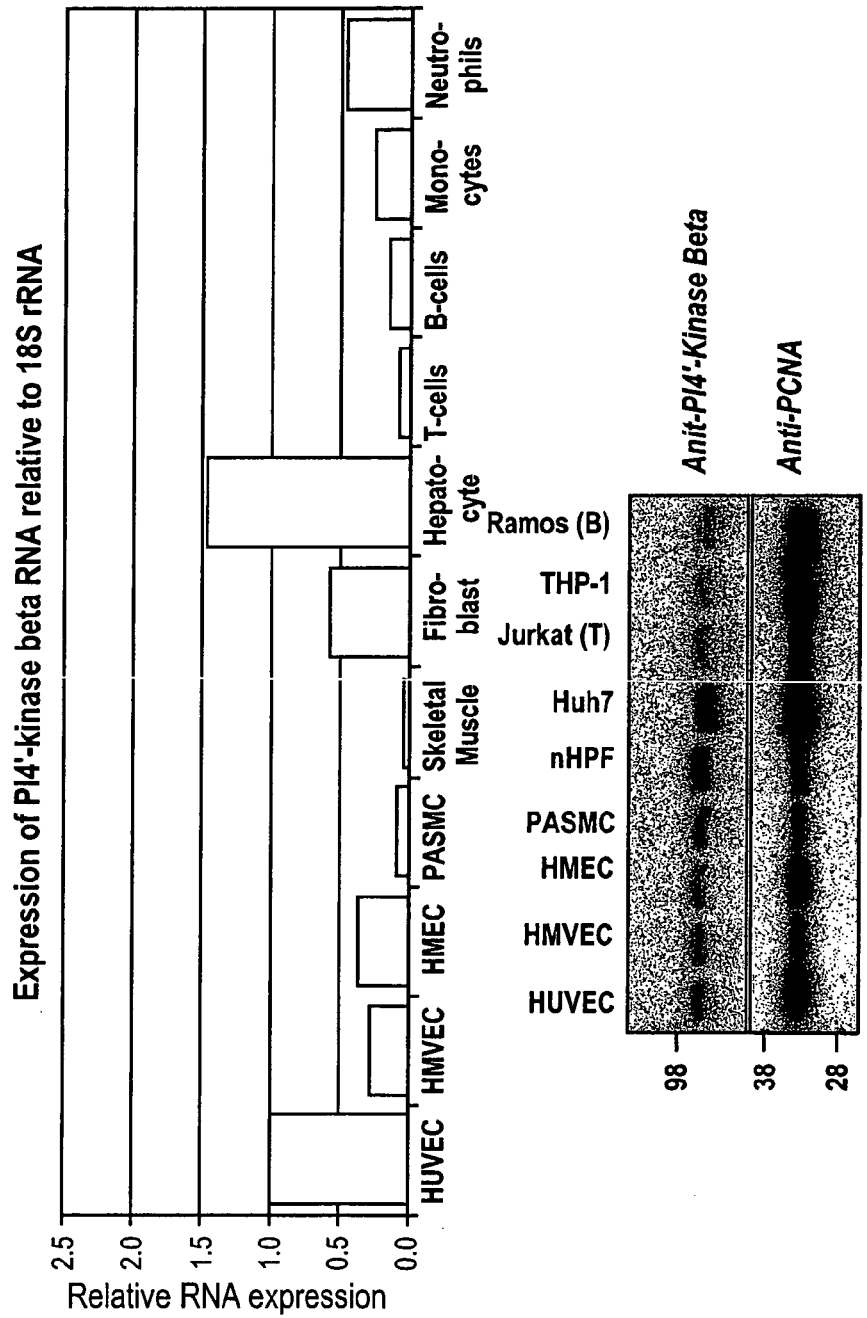
FIG. 13 shows mRNA and protein expression of PI4'-kinase beta RNA.
Figure 14:
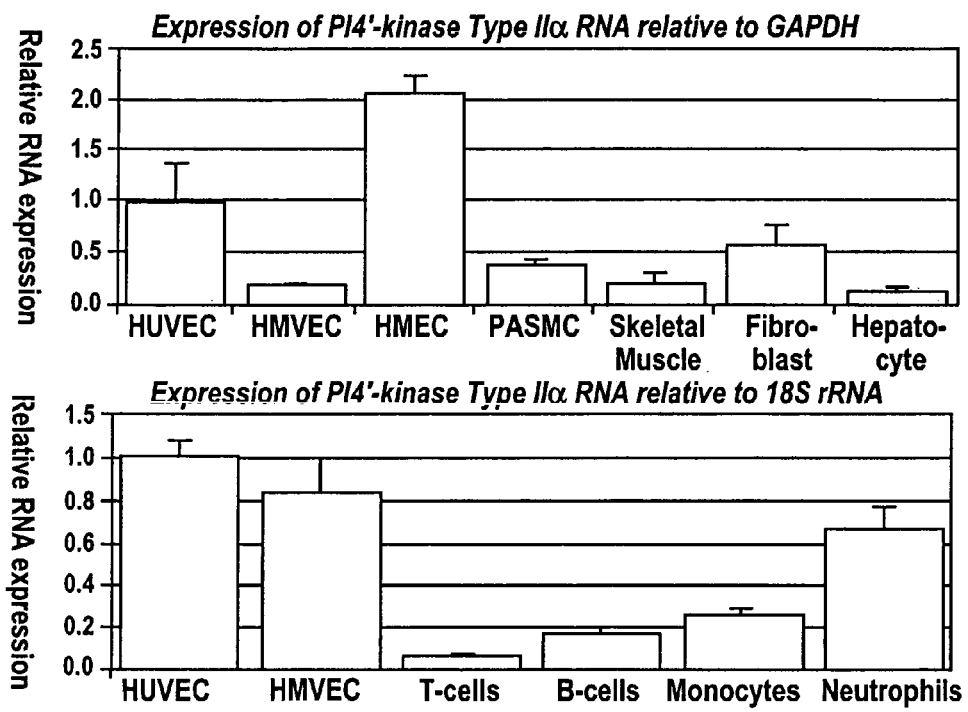
FIG. 14 shows mRNA expression of PI4'-kinase type II α RNA.
Figure 15:
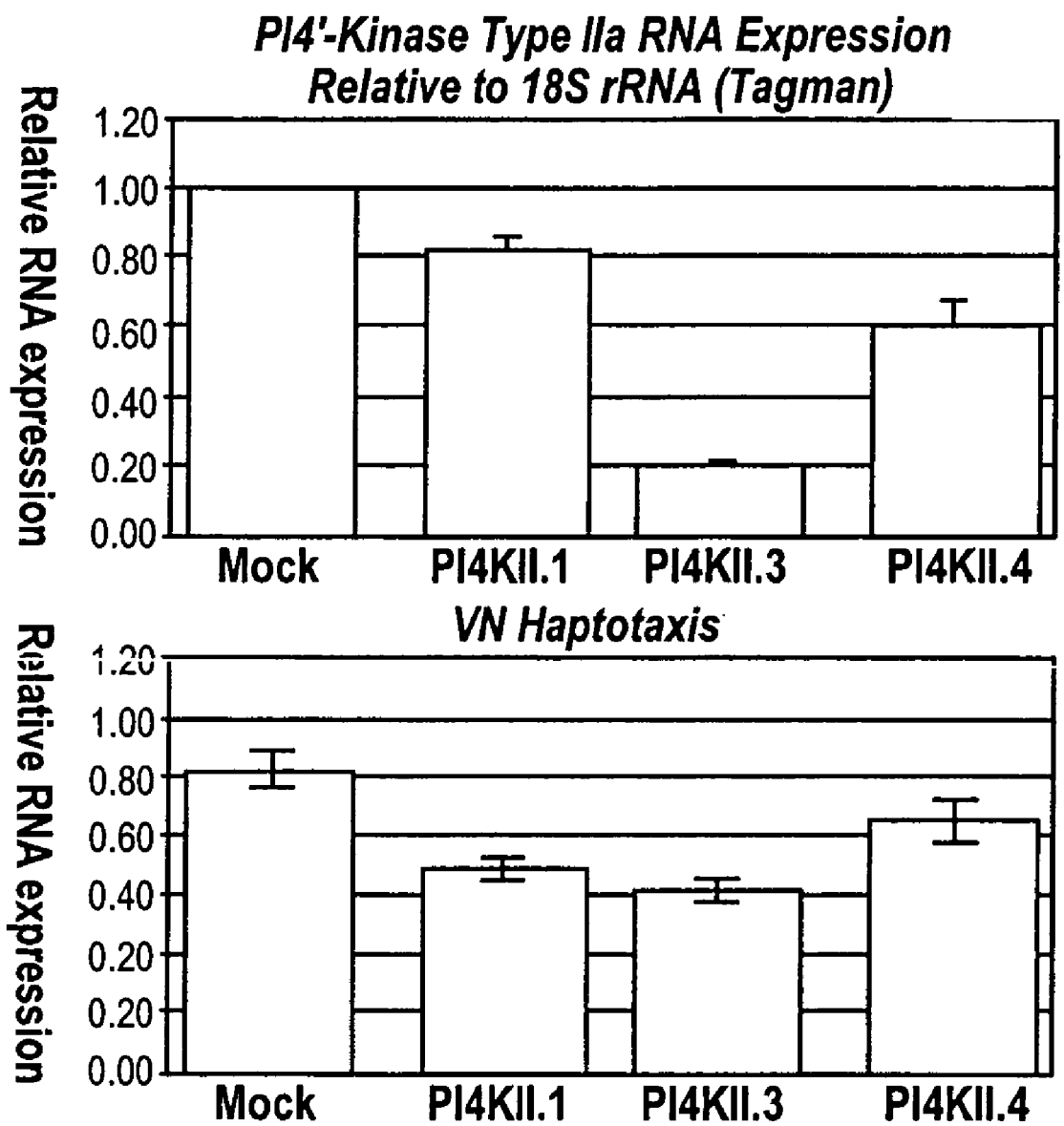
FIG. 15 shows that PI4'-kinase type II α RNAi inhibits VN haptotaxis.

Identification of Genes Involved in Modulation of Angiogenesis and tumorigenesis in Vitro Using a Haptotaxis Assay Using a retroviral base system, complex libraries of cDNAs and GFP-fusions have been expressed in human primary endothelial cells (e.g., HUVECS) (See FIGS. 1 and 2). Cells that switch to a differentiated angiostatic state can be identified. The cells are then assayed for migration along a haptotactic gradient of specific matrix proteins such as vitronectin and fibronectin in a Boyden chamber assay. Cells were selected for impaired haptotaxis (see, e.g., Klemke et al., *J. Cell Biol*. 4:961-972 (1998)). cDNAs derived from the following hits were identified using this screen: phosphatidylinositol 4-kinase beta (SEQ ID NO:2), phosphatidylinositol 4-kinase type II (SEQ ID NO:4), MAP/ERK kinase kinase 3 (SEQ ID NO:6), SHIP2 inositol phosphatase (SEQ ID NO:8), delta7-sterol reductase (SEQ ID NO:29), protein geranylgeranyltransferase type I (SEQ IDNO:9), glucosamine-6-sulfatase (SEQ ID NO11, carbohydrate sulfotransferase 1 (CHST1) (SEQ ID NO: 13), heat shock protein 105 kDa beta (SEQ ID NO: 15), UCH-L1 ubiquitin carboxyl-terminal hydrolase (SEQ ID NO: 17), ubiquitin-conjugating enzyme E2M (SEQ ID NO:31), equilibrative nucleoside transporter 1 (hENT1/SLC29A1) (SEQ ID NO:19), novel LIV-1-related 6 TM protein (6TM ZIP zinc transporter domain) (SEQ ID NO:21), frizzled-4 (SEQ ID NO:22), stathmin 1/oncoprotein 1 adaptor (SEQ ID NO:23), and Homo sapiens RNA-binding protein G3BP-2 (SEQ ID NOS:25 and 27).

The sequence listing below provides exemplary nucleic acid and protein accession numbers for the proteins corresponding to the cDNAs identified in the haptotaxis assay (SEQ ID NOS:2, 4, 6, 8, 9, 11, 13, 15, 17, 19, 21-23, 25, 27, 29 and 31). Also provided are the sequences of the cDNAs identified in the screening assay (SEQ ID NOS:1, 3, 5, 7, 8, 10, 12, 14, 16, 18. 20, 22-24, 26, 28 and 30). The orientation of the cDNAs identified in the screen is provided in FIG. 3.

Example 2

Identification of Genes Involved in Modulation of Angiogenesis and Tumorigenesis in vivo This study in mice is designed to provide information on the growth and angiogenic characteristics of MDA-MB-231 cells infected with a target as described herein or an isogenic negative control and implanted subcutaneously in mice (Strain: CB-17 scid). MDA-MB-231 (wt) cells will also be implanted and measured. Tumor Cell Injection Density: $1 \times 10^7$ per injection site (shaved right hind flank). See FIG. 16.

When tumors reach a diameter of approximately 1 cm, animals are randomly divided into subgroups according to tumor size using a stratified randomization method (Day 0). Tumors in selected subgroups are resected by survival surgery and fixed in formalin and the animals will be observed for signs of metastasis via changes in body weight and/or clinical signs. Animals showing any of these signs in severity are terminated and the lungs, liver, sternum, femur, and lymph nodes (axial and mesenteric) are harvested and fixed in 10% buffered formalin for histological examination. Tumors in remaining subgroups will continue to be measured until they reach 2,000 mm3.

The mean tumor volume for each group was calculated for each time point. Comparisons between groups at specific times are made using an unpaired, two-tailed t-test, and the results analyzed using analysis of variance (ANOVA) or the student's t-test. Differentials in tumor growth between groups are determined by calculating volume-doubling time (VDT), or by determining the survival time.

Example 3

Identification of Genes Involved in Modulation of Angiogenesis in vitro Using a VEGF-R2 Assay Using a retroviral system, complex libraries of cDNAs are expressed in human primary endothelial cells (e.g., HUVECS, Clonetic CC-2519). HUVEC cells that switch to a differentiated angiostatic state can be identified using a VEGFR2 internalization assay. After infection with a retroviral cDNA library, cells are seeded in EGM-2 media (Clonetics EGM-2 bullet kit CC-3162) and grown to log phase. Cells are cultured in starvation medium (EGMS with 0.1% FCS plus 1% BSA in place of VEGF and FCS) at 37° C. for 16 hours. The starved HUVECs are stimulated with VEGF stimulation medium at 37° C. for 1.5 hours, trypsinized, and stained with VEGFR2 antibody. Single cells exhibiting increased VEGF-R2 expression (i.e., blocked or inhibited receptor internalization) are selected using FACS analysis.

Co-culture of HUVECs on smooth muscle cells can be used to confirm that genes identified via VEGR2 internalization are genes that encode angiogenesis proteins. Smooth muscle cells (Clonetics Pulmonary Artery SMCs CC-2581) are plated at 40,000 cells per well of a collagen coated 24 well tissue culture plate and grown to confluency. HUVECs are plated onto the smooth muscle cells at 22,000 cells per well. The phenotype of vascular bed formation is determined as follows: photographs are taken and formation of tubular morphology of the HUVECs is determined empirically. The co-culture assay is typically used to confirm an anti-angiogenic phenotype.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that inhibits cell migration or haptotaxis, the method comprising the steps of:
   (i) contacting the compound with an endothelial cell comprising a human phosphatidylinositol 4-kinase type II;
   (ii) determining the functional effect of the compound upon migration of said endothelial cell or haptotaxis along a vitronectin or fibronectin gradient; and
   (iii) determining the effect of the compound upon phosphatidylinositol 4-kinase type II kinase enzyme activity, wherein a decrease in said haptotaxis or of said migration and a decrease in kinase activity, as compared to an untreated control, identifies the compound as an inhibitor of cell migration or haptotaxis.

2. The method of claim 1, wherein the cell migration is determined by measuring haptotaxis along the vitronectin gradient.

3. The method of claim 1, wherein the human phosphatidylinositol 4-kinase type II is recombinant.

4. The method of claim 1, wherein the compound is an antibody.

5. The method of claim 1, wherein the compound is an antisense molecule.

6. The method of claim 1, wherein the compound is an RNAi molecule.

7. The method of claim 1, wherein the compound is a small organic molecule.

8. The method of claim 1, wherein said cell migration is measured using a Boyden chamber.

* * * * *

SEQUENCE LISTING

<160> NUMBER OF SEQ ID NOS: 32

<210> SEQ ID NO 1
<211> LENGTH: 344
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 1
cagcaaggtt ctcagcttcc ttgcttccat ggctccagca ccattcgaaa cctcaaagag      60
aggttccaca tgagcatgac tgaggagcag ctgcagctgc tggtggagca gatggtggat     120
ggcagtatgc ggtctatcac caccaaactc tatgacggct ccagtacct caccaacggc     180 atcatgtgac acgctcctca gcccagagtg gtgggggtc cagggcaccc tccctagagg     240
gcccttgtct gagaaacccc aaaccaggaa accccaccta cccaccatcc acccagggaa     300
atggaaggca agaaacacga aggatcatgt ggtaactgcg agag                       344

<210> SEQ ID NO 2
<211> LENGTH: 347
<212> TYPE: DNA
<213> ORGANISM: Homo sapiens
<220> FEATURE:
<223> OTHER INFORMATION: phosphatidylinositol 4-kinase beta cDNA

<400> SEQUENCE: 2
cagcaaggtt ctcagcttcc ttgcttccat ggctccagca ccattcgaaa cctcaaagag      60
aggttccaca tgagcatgac tgaggagcag ctgcagctgc tggtggagca gatggtggat     120
ggcagtatgc ggtctatcac caccaaactc tatgacggct ccagtacct caccaacggc     180 atcatgtgac acgctcctca gcccaggagt ggtgggggt ccagggcacc ctccctagag     240
ggcccttgtc tgagaaaccc caaaccagga accccacct acccaaccat ccacccaagg     300
gaaatggaag caagaaaaca cgaaggatca tgtggtaact gcgagag                   347

<210> SEQ ID NO 3
<211> LENGTH: 252
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 3
ggccagtgtc cgagttcagc tgcatgtgat tgtcggggct gggattgggg caggcaggcg      60
agctgtacct tcgtccacag ggcatgcaca tccagctctc agaaattctt cctgtcagcc     120
aggtggaagc ccgggacaag tggactcttg gtggctggac tggaagggga ccggcgggga     180
ccagcctgga ccagctgacc agagggctgc acatctctgc tctgcagcag ggcaagcaga     240
ggacatgcag cc                                                          252

<210> SEQ ID NO 4
<211> LENGTH: 251
<212> TYPE: DNA
<213> ORGANISM: Homo sapiens
<220> FEATURE:
<223> OTHER INFORMATION: phosphatidylinositol 4-kinase type II (PI4KII)
      cDNA

```
<400> SEQUENCE: 4
ggccagtgtc cgagtcagct gcatgtgatt gtcggggctg ggattggggc aggcaggcga      60
gctgtacctt cgtccacagg gcatgcacat ccagctctca gaaattcttc ctgtcagcca     120
ggtggaagcc cgggacaagt ggactcttgg tggctggact ggaaggggac cggcggggac     180
cagcctggac cagctgacca gagggctgca catctctgct ctgcagccgg gcaagcagag     240
gacatgcagc c                                                          251

<210> SEQ ID NO 5
<211> LENGTH: 339
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 5
ctggttttgc agaagtgtgt gtcgcatgcg ccagttgggc ctggaccctc ctgtgtccat      60
ccctgttccc ccaggggctc tatcagcccc tgtaccccac actgccctct gaagacacac     120
aggctcctgc ttccacctcg gcccttgccc agggtggggc ctggccctca tcttgaccaa     180
agctgctgtg tggcagctcg gcctctctac gaccccatct tggtggctgc acactcttcc     240
tggcccgcac cccatcccc agtccctgtt ccccaagagg atacagagca cggtgcttgc     300
tgactcaact gtgcgtccca tgttcagggt cttacagag                            339

<210> SEQ ID NO 6
<211> LENGTH: 340
<212> TYPE: DNA
<213> ORGANISM: Homo sapiens
<220> FEATURE:
<223> OTHER INFORMATION: mitogen-activated protein MAP/ERK kinase kinase
      kinase 3 (MAP3K3) cDNA

<400> SEQUENCE: 6
ctggttttgc agaagtgtgt gtcgcatgcg ccagttgggc ctggaccctc ctgtgtccat      60
ccctgttccc ccaggggctc tatcagcccc tgtaccccac actgccctct gaagacaaca     120
caggctcctg cttccacctc ggcccttgcc cagggtgggg cctggccctc atcttgacca     180
aagctgctgt gtggcagctc ggcctctcta cgaccccatc ttggtggctg cacactcttc     240
ctggcccgca cccccatccc cagtccctgt tccccaagag gatacagagc acggtgctgg     300
ctgactcaac tgtgcgtccc aggttcaggg tcttacagag                           340

<210> SEQ ID NO 7
<211> LENGTH: 218
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 7
ggggagggag atgcacctta atattattgg ggttggttgg ggtggggcag gatctcagcc      60
ataaagtgcc agtttgctta gttctcactg tctcctggtc tgtgctgccc tgctctgggg     120
atgcacggcg gcagggtggg ggaggaggt tcctcgcagg tctcagcccg ggacagggtc     180
ttgcaagcag cctcctgggc agtcgtaagg gttacggc                             218

<210> SEQ ID NO 8
```

```
<211> LENGTH: 217
<212> TYPE: DNA
<213> ORGANISM: Homo sapiens
<220> FEATURE:
<223> OTHER INFORMATION: SHIP2 inositol phosphatase, inositol
      polyphosphate phosphatase-like 1 (INPPL1) cDNA

<400> SEQUENCE: 8
ggggagggag agcaccttaa tattattggg gttggttggg gtggggcagg atctcagcca      60
taaagtgcca gtttgcttag ttctcactgt ctcctggtct gtgctgccct gctctgggga     120
tgcacggcgg cagggtgggg gagggaggtt cctcgcaggt ctcagcccgg gacagggtct     180
tgcaagcagc ctcctgggca gtcgtaaggg ttgcggc                              217

<210> SEQ ID NO 9
<211> LENGTH: 270
<212> TYPE: DNA
<213> ORGANISM: Homo sapiens
<220> FEATURE:
<223> OTHER INFORMATION: cDNA sequence identified in human primary
      endothelial cell haptotaxis assay; protein
      geranylgeranyltransferase type I beta subunit cDNA

<400> SEQUENCE: 9
ccaggtatga agagcctcgg aaaccacagc gatttagatt tgatctgtct tctgtgggaa      60
ggacctgcag ggaataaatc cactctatta tatcatcttt gttcaccaca tctaaggaat     120
ccaacatatc cagcccggag agtgcaaaaa atgcaattgt caacctgctt gtctcgagtg     180
aagaatagcg ctccggcaaa acctggaggc agcgctggaa aaatcgcacg tgccgatccc     240
gtaagaaatc cagccgctct ccctcaccgc                                      270

<210> SEQ ID NO 10
<211> LENGTH: 174
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 10
acgtgttgtc cagctcgccc gtctcaacca gcatgttgta aatcgtctcc atggagtcgt      60
caccgacatg agggtctgca agcgcttccg ctggagcatg ttggtgaatt ccatgtggat     120
gggcttcatg ggccccgtgt agcgcatgat ccagtgtttg tccgggttgg gcgc           174

<210> SEQ ID NO 11
<211> LENGTH: 175
<212> TYPE: DNA
<213> ORGANISM: Homo sapiens
<220> FEATURE:
<223> OTHER INFORMATION: glucosamine-6-sulfatase, extracellular
      sulfatase SULF-2 cDNA

<400> SEQUENCE: 11
acgtgttgtc cagctcgccc gtctcaacca gcatgttgta aatcgtctcc atggagtcgt      60
ccaccgacat gagggtctgc aagcgcttcc gctggagcat gttggtgaat tccatgtgga     120
tgggcttcat gggccccgtg tagcgcatga tccagtgttt gtccgggttg ggcgc          175

<210> SEQ ID NO 12
<211> LENGTH: 458
<212> TYPE: DNA
<213> ORGANISM: Homo sapiens
<220> FEATURE:
```

<223> OTHER INFORMATION: cDNA sequence identified in human primary
      endothelial cell haptotaxis assay

<400> SEQUENCE: 12

| agcttggagc agtccctctt tgacctcacc ccttggagaa gcagcccat gaaggtgccc | 60 |
| agccatgcaa tgttcctgga aggccgtcct cctccttgcc ctggcctcca ttgccatcca | 120 |
| gtacacggcc atccgcacct tcaccgccaa gtcctttcac acctgccccg ggctggcaga | 180 |
| ggccgggctg gccgagcgac tgtgcgagga gagccccacc ttcgcctaca acctctcccg | 240 |
| caagacccac atcctcatcc tggccaccac gcgcagcggc tcctccttcg tgggccagct | 300 |
| cttcaaccag cacctggacg tcttctacct gtttgagccc ctctaccacg tccagaacac | 360 |
| gctcatcccc cgcttcaccc aggggcaaga gcccggccga ccggcgggtc atgctaggcg | 420 |
| ccagccgcga cctcctgcgg agcctctacg actgcgac | 458 |

<210> SEQ ID NO 13
<211> LENGTH: 457
<212> TYPE: DNA
<213> ORGANISM: Homo sapiens
<220> FEATURE:
<223> OTHER INFORMATION: carbohydrate sulfotransferase 1, carbohydrate
      (keratan sulfate Gal-6) sulfotransferase 1 (CHST1)
      cDNA

<400> SEQUENCE: 13

| agcttggagc agtccctctt tgacctcacc ccttggagaa gcagcccat gaaggtgccc | 60 |
| agccatgcaa tgttcctgga aggccgtcct cctccttgcc ctggcctcca ttgccatcca | 120 |
| gtacacggcc atccgcacct tcaccgccaa gtcctttcac acctgccccg ggctggcaga | 180 |
| ggccgggctg gccgagcgac tgtgcgagga gagccccacc ttcgcctaca acctctcccg | 240 |
| caagacccac atcctcatcc tggccaccac gcgcagcggc tcctccttcg tgggccagct | 300 |
| cttcaaccag cacctggacg tcttctacct gtttgagccc ctctaccacg tccagaacac | 360 |
| gctcatcccc cgcttcaccc agggcaagag cccggccgac cggcgggtca tgctaggcgc | 420 |
| cagccgcgac ctcctgcgga gcctctacga ctgcgac | 457 |

<210> SEQ ID NO 14
<211> LENGTH: 526
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 14

| tgaaggggtc atgaatgctc ggccatgaaa tctttgaagt tagacaccgt atgtttgcat | 60 |
| gagtgatttg ctgattttgg ctgcaactcc gattgttcta ttttttgatc caaatgatat | 120 |
| agactgacgg ggtgcaccgg tcgctgaact cattggcgat ggtctcgatg cccccggccc | 180 |
| gggctaccgc gatgtagcag ctctgcgagc ccacgtccaa ccccaccacc gacatggccg | 240 |
| gctcgcggtc cgcctccgcc tcgggtctcg gtctacgtcc tccggccccc tgcctgcttc | 300 |
| tcctgccgcc gctttctgcc ctggccgcgt tctgctccgg cccgcggggt ctggccgttc | 360 |
| ctctgacact cagaaggaca cacagaccgc cgcggcctgt caggagcctc ctactccccc | 420 |
| ggggacagcg gcggctggct gataagaaac cctgggagaa gcggggctc agcctccgca | 480 |
| ggtcgctccg cacctcgggt tgcctgcctc actctgccgc ggctcg | 526 |

```
<210> SEQ ID NO 15
<211> LENGTH: 529
<212> TYPE: DNA
<213> ORGANISM: Homo sapiens
<220> FEATURE:
<223> OTHER INFORMATION: heat shock protein 105kDa beta cDNA

<400> SEQUENCE: 15
tgaaggggtc attgaatgct cggccatgaa atcttttgaa gttagacacc gtattgtttg        60
catgagtgat ttgctgattt ttggctgcaa ctccgattgt tctattttt gatccaaatg       120 atatgactga cggggtgcac cggtcgctga actcattggc gatggtctcg atgccccgg       180 cccgggctac cgcgatgtag cagctctgcg agcccacgtc caaccccacc accgacatgg       240
ccggctcgcg gtccgcctcc gcctcgggtc tcggtctacg tcctccggcc cctgcctgc       300 ttctcctgcc gccgctttct gccctggccg cgttctgctc cggcccgcgg ggtctggccg       360
ttcctctgac actcagaagg acacacagac agccgcggcc tgtcaggagc tcctactcc       420 cccggggaca gcggcggctg gctgataaga aaccctggga gaaagcgggg ctcagcctcc       480
gcaggtcgct ccgcacctcg ggttgcctgc ctcactctgc cgcggctcg                   529

<210> SEQ ID NO 16
<211> LENGTH: 317
<212> TYPE: DNA
<213> ORGANISM: Homo sapiens
<220> FEATURE:
<223> OTHER INFORMATION: cDNA sequence identified in human primary
      endothelial cell haptotaxis assay
<220> FEATURE:
<221> NAME/KEY: modified_base
<222> LOCATION: (23)..(29)
<223> OTHER INFORMATION: n = g, a, c or t

<400> SEQUENCE: 16
actgaagcat tttagactgc atnnnnnnnt atatattttc atgttgaagg gaagagggga        60
aatcagcaaa gtccctccca cagagcatta ggctgccttg cagagagcca cggcagagaa       120
gcggacttct ccttgctcac gctcggtgaa ttctctgcag accttggcag cgtccttcag       180
cagggtgtcc tctgaactgg cgccatggtt caccggaaaa ggcattcgtc catcaagtta       240
tagaggtggc atccacgttg ttaaacagaa taaaatggaa attcaccttg tcatctaccc       300
gacattggcc ttcctgt                                                      317

<210> SEQ ID NO 17
<211> LENGTH: 319
<212> TYPE: DNA
<213> ORGANISM: Homo sapiens
<220> FEATURE:
<223> OTHER INFORMATION: UCH-L1 ubiquitin carboxyl-terminal hydrolase,
      ubiquitin carboxyl-terminal esterase L1 (ubiquitin
      thiolesterase) (UCHL1) cDNA

<400> SEQUENCE: 17
actgaagcat tttagactgc atggggggt atatattttc atgttgaagg gaagagggga        60
aatcagcaaa gtccctccca cagagcatta ggctgccttg cagagagcca cggcagagaa       120
gcggacttct ccttgctcac gctcggtgaa ttctctgcag accttggcag cgtccttcag       180
cagggtgtcc tctgaactgg cgccatggtt caccggaaaa ggcattcgtc catcaagttc       240
atagaggtgg ccatccacgt tgttaaacag aataaaatgg aaattcacct tgtcatctac       300
ccgacattgg ccttcctgt                                                    319
```

```
<210> SEQ ID NO 18
<211> LENGTH: 161
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 18
ggtaagaact gggcatgggg agttcgggag ggggacatgg agagaacaca gaggaggagg     60
cgcaggggga gaatggagta tatcaggtca aaccatacaa cggtcagacc cagctcctag    120
ccactccagt gacaggcaga cagtctgaca gacacggacg c                        161

<210> SEQ ID NO 19
<211> LENGTH: 158
<212> TYPE: DNA
<213> ORGANISM: Homo sapiens
<220> FEATURE:
<223> OTHER INFORMATION: equilibrative nucleoside transporter 1, solute
      carrier family 29 (nucleoside transporters),
      member 1 cDNA

<400> SEQUENCE: 19
ggtaagaact gggcatgggg agttgggagg gggacatgga gagaacacag aggaggaggc     60 gcagggggaga atggagtata tcaggtcaaa ccatacaacg gtcagaccca gctcctagcc   120
accccaggac aggcagacag tctgacagac acggacgc                            158

<210> SEQ ID NO 20
<211> LENGTH: 262
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 20
gctctggcga ttggaaccct ctactccaac gccctcttcc agctcatccc ggagcatttg     60
gtttcaaccc tcttgaaaga ttattatgtc tccaagtctg cagtggtgtt tgggggcttt    120
tatcttttct ttttcacaga gaagatcttg aagattcttc ttaagcagaa aaatgagcat    180
catcatggac acagccatta tgcctctagt cgcttccctc agaaggacc aggaggaggg     240 ggtgatggag aagccgcaga ac                                             262

<210> SEQ ID NO 21
<211> LENGTH: 264
<212> TYPE: DNA
<213> ORGANISM: Homo sapiens
<220> FEATURE:
<223> OTHER INFORMATION: novel LIV-1-related6TM protein (6TM ZIP zinc
      transporter domain) cDNA

<400> SEQUENCE: 21
gctctggcga ttggaaccct ctactccaac gccctcttcc agctcatccc ggaggcattt     60
ggtttcaacc ctctggaaga ttattatgtc tccaagtctg cagtggtgtt tgggggcttt    120
tatcttttct ttttcacaga gaagatcttg aagattcttc ttaagcagaa aaatgagcat    180
catcatggac acagccatta tgcctctgag tcgcttccct ccaagaagga ccaggaggag    240
ggggtgatgg agaagctgca gaac                                           264

<210> SEQ ID NO 22
<211> LENGTH: 109
```

```
<212> TYPE: DNA
<213> ORGANISM: Homo sapiens
<220> FEATURE:
<223> OTHER INFORMATION: cDNA sequence identified in human primary
      endothelial cell haptotaxis assay; WNT receptor
      Frizzled-4 (FZD4) cDNA

<400> SEQUENCE: 22
ctttctgttg ctgtctcttg ccatgcactt gtgcggtgat tacacacttg acagtaccag     60
gagacaaatg acttacagat cccccgacat gcctcttccc cttggcaag               109

<210> SEQ ID NO 23
<211> LENGTH: 162
<212> TYPE: DNA
<213> ORGANISM: Homo sapiens
<220> FEATURE:
<223> OTHER INFORMATION: cDNA sequence identified in human primary
      endothelial cell haptotaxis assay; stathmin cDNA

<400> SEQUENCE: 23
actgtattgg ctctgtgaaa acatatttgt gaaaagagta tgtagtggct tcttttgaac     60
tgttagatgc tgaatatctg ttcactttc aatcccaatt ctgtcccaat cttaccagat    120
gctactggac ttgaatggtt aataaaactg cacagtgctg tt                     162

<210> SEQ ID NO 24
<211> LENGTH: 632
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 24
ggctcaggtt caggttcatg agaggattct tccaaaggct cctctatgcc attagtcaca     60
ggggtgagct tcatagtaac cactgttagc atttttcttgc acaggttcag gagatggttg   120
tctttcttct tgttcctctt ctactttatc ttctgattct tcatcaagtt caggctcaga   180
atcaccaaac acttcatctt cataacgaaa catatcattg tgaacattaa atttatttgg   240
aacagatcct tcaggagccc gaaccaaggt ttgcctaaac ttttctttct ggttgtccac   300
tgtttgacag caaacccatg acctggacaa ctactccctc actcacggtt gccttgagac   360
tttccccttg acgaatattt agtatgactt tcactgaagt ttcagagata atactttgtg   420
gtgtatatca ttttggccat aaacagcttc ctggggcttt ccactagcat ctactccacc   480
atgaacatag gaagaattcc tgccaataaa aacctggtgt taaatattcc cggagcttta   540
ttcagcaagg tataatattt gcctcacaaa actcccgcct tacaagcagc ggactgggct   600
tctccataac catttccttg ctgccaatgt ca                                 632

<210> SEQ ID NO 25
<211> LENGTH: 619
<212> TYPE: DNA
<213> ORGANISM: Homo sapiens
<220> FEATURE:
<223> OTHER INFORMATION: RNA-binding protein 3BP-2, Ras-GTPase
      activating protein (GAP[21 120[22 ), SH3 domain-binding protein 2
      (KIAA0660) cDNA

<400> SEQUENCE: 25
ggctcaggtt caggttcatg agaggattct tccaaaggct cctctatgcc attagtcaca     60
gggtgagctt catagtaacc actgttagca ttttcttgca caggttcagg agatggttgt   120
```

```
ctttcttctt gttcctcttc tacttcatct tctgattctt catcaagttc aggctcagaa        180
tcaccaaaca cttcatcttc ataacgaaac atatcattgt gaacataaaa tttatttgga        240
acagatcctt caggagccag aacaaaggtt tgcataaact ttctttctgg ttgtccactg        300
ttagacagca aacccatgac ctggacaact actccatcac tcaaggttgc atgagcatcc        360
acatgacgaa ttttagtatg acattcactg aagttcagag ataatacttt gtggtgtata        420
tcattttggc cataaacagc ttcctggggc tttccactag catctactcc accatgaaca        480
taggaagaat tcctgccata aaacctgtgt aaatattccg gagctttatt cagcaaagta        540
taatattgcc tcacaaactc ccgccctaca agcagcggac tgggcttctc cataaccatt        600
tctttgctgc acaatgtca                                                     619
```

<210> SEQ ID NO 26
<211> LENGTH: 259
<212> TYPE: DNA
<213> ORGANISM: Homo sapiens
<220> FEATURE:
<223> OTHER INFORMATION: cDNA sequence identified in human primary
      endothelial cell haptotaxis assay
<220> FEATURE:
<221> NAME/KEY: modified_base
<222> LOCATION: (247)
<223> OTHER INFORMATION: n = g, a, c or t

<400> SEQUENCE: 26

```
gtcgcacgtc gcagcgcctg gcgcccggga aaaggtggtt gtgaggcaga cgaactcgcg        60
gctctccggc ttccgaggct tccgagattg tcggaggaag ggggcggcga acaataaga        120 acccgccgca cccggtcctc agcgactctt ctgacctccg cgcgacgtac ccgccgccgc        180
cgttgctgga gcatttgaca ttgtgcagca agaaatggtt tggagaagcc cagtccgctc        240
ttgtaangcg ggagtttgt                                                     259
```

<210> SEQ ID NO 27
<211> LENGTH: 261
<212> TYPE: DNA
<213> ORGANISM: Homo sapiens
<220> FEATURE:
<223> OTHER INFORMATION: RNA-binding protein 3BP-2, Ras-GTPase
      activating protein (GAP[21 120[22 ), SH3 domain-binding protein 2
      (KIAA0660) cDNA

<400> SEQUENCE: 27

```
gtcgcacgtc gcagcgcctg gcgcccggga agaggtggtt gtgaggcaga cgaactcgcg        60
gctctccggc ttccgaggct tccgagttgt cggaggaagg gggcggcgag caataagaac        120
ccgccgcacc cggtcctcag cgactcttct gacctccgcg cgacgtaccc gccgccgccg        180
ttggctggag catttgacat tgtgcagcaa agaaatggtt atggagaagc ccagtccgct        240
gcttgtaggg cgggagtttg t                                                  261
```

<210> SEQ ID NO 28
<211> LENGTH: 144
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 28

```
ctctggtttg caaacgctca tctcctgtcc tggttctcgc ccaccatcat cttcgacaac        60
tggatcccac tgctgtggtg cgccaacatc cttggctatg ccgtctccac cgttcgccat        120
```

```
ggtcgagggc tacttcttcc ccac                                          144
```

<210> SEQ ID NO 29
<211> LENGTH: 143
<212> TYPE: DNA
<213> ORGANISM: Homo sapiens
<220> FEATURE:
<223> OTHER INFORMATION: delta7-sterol reductase, 7-dehydrocholesterol
      reductase (DHCR7) cDNA

<400> SEQUENCE: 29

```
ctctggtttg caaacgctca tctcctgtcc tggttctcgc ccaccatcat cttcgacaac    60
tggatcccac tgctgtggtg cgccaacatc cttggctatg ccgtctccac cttcgccatg   120
gtcaagggct acttcttccc cac                                          143
```

<210> SEQ ID NO 30
<211> LENGTH: 158
<212> TYPE: DNA
<213> ORGANISM: Homo sapiens
<220> FEATURE:
<223> OTHER INFORMATION: cDNA sequence identified in human primary
      endothelial cell haptotaxis assay

<400> SEQUENCE: 30

```
ggcccccagg attcccccag ccaaactgtc tttgtcacca cgtggggctc acttttcatc    60
cttccccaac ttccctagtc cccgtactag ttggacagcc cccttcggct acaggaaggc   120 aggagggtg agtcccctac tccctcttca ctgtggcc                            158
```

<210> SEQ ID NO 31
<211> LENGTH: 159
<212> TYPE: DNA
<213> ORGANISM: Homo sapiens
<220> FEATURE:
<223> OTHER INFORMATION: ubiquitin conjugating enzyme E2M cDNA

<400> SEQUENCE: 31

```
ggcccccagg attcccccag ccaaactgtc tttgtcacca cgtggggctc acttttcatc    60
cttccccaac ttccctagtc cccgtactag gttggacagc ccccttcggc tacaggaagg   120
caggaggggt gagtccccta ctccctcttc actgtggcc                          159
```

<210> SEQ ID NO 32
<211> LENGTH: 200
<212> TYPE: PRT
<213> ORGANISM: Artificial Sequence
<220> FEATURE:
<223> OTHER INFORMATION: Description of Artificial Sequence:synthetic
      poly Gly flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 32

```
Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly
                 20                  25                  30

Gly Gly Gly Gly Gly Gly Gly Gly Gly Gly Gly Gly Gly Gly Gly
             35                  40                  45

Gly Gly Gly Gly Gly Gly Gly Gly Gly Gly Gly Gly Gly Gly Gly
```

-continued

```
            50                  55                  60
Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
             85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
            195                 200
```